(12) United States Patent
Pradeep et al.

(10) Patent No.: US 8,533,042 B2
(45) Date of Patent: *Sep. 10, 2013

(54) NEURO-RESPONSE STIMULUS AND STIMULUS ATTRIBUTE RESONANCE ESTIMATOR

(75) Inventors: Anantha Pradeep, Berkeley, CA (US); Robert T. Knight, Berkeley, CA (US); Ramachandran Gurumoorthy, Berkeley, CA (US)

(73) Assignee: The Nielsen Company (US), LLC, Schaumburg, IL (US)

( * ) Notice: Subject to any disclaimer, the term of this patent is extended or adjusted under 35 U.S.C. 154(b) by 179 days.

This patent is subject to a terminal disclaimer.

(21) Appl. No.: 12/182,874

(22) Filed: Jul. 30, 2008

(65) Prior Publication Data

US 2009/0036756 A1   Feb. 5, 2009

Related U.S. Application Data

(60) Provisional application No. 60/952,723, filed on Jul. 30, 2007.

(51) Int. Cl.
*G06Q 30/00* (2012.01)

(52) U.S. Cl.
CPC ..................................... *G06Q 30/00* (2013.01)
USPC .................................... 705/14.42; 705/14.52

(58) Field of Classification Search
CPC ..................................................... G06Q 30/00
USPC .......................................... 705/14.41, 14.66
See application file for complete search history.

(56) References Cited

U.S. PATENT DOCUMENTS

| | | | |
|---|---|---|---|
| 2,549,836 | A | 4/1951 | McIntyre et al. |
| 3,490,439 | A | 1/1970 | Rolston |
| 3,572,322 | A | 3/1971 | Wade |
| 3,735,753 | A | 5/1973 | Pisarski |
| 3,880,144 | A | 4/1975 | Coursin et al. |
| 3,901,215 | A | 8/1975 | John |
| 3,998,213 | A | 12/1976 | Price |
| 4,075,657 | A | 2/1978 | Weinblatt |
| 4,149,716 | A | 4/1979 | Scudder |

(Continued)

FOREIGN PATENT DOCUMENTS

| | | |
|---|---|---|
| GB | 1374658 | 11/1974 |
| GB | 2221759 | 2/1990 |

(Continued)

OTHER PUBLICATIONS

Unknown, Illustrated Dictionary of Science, Andromeda, 1988, Electroencephalograph definition.*

(Continued)

*Primary Examiner* — Ella Colbert
*Assistant Examiner* — Scott S Trotter
(74) *Attorney, Agent, or Firm* — Hanley, Flight & Zimmerman, LLC

(57) ABSTRACT

A system determines neuro-response stimulus and stimulus attribute resonance. Stimulus material and stimulus material attributes such as communication, concept, experience, message, images, audio, pricing, and packaging are evaluated using neuro-response data collected with mechanisms such as Event Related Potential (ERP), Electroencephalography (EEG), Galvanic Skin Response (GSR), Electrocardiograms (EKG), Electrooculography (EOG), eye tracking, and facial emotion encoding. Neuro-response data is analyzed to determine stimulus and stimulus attribute resonance.

29 Claims, 8 Drawing Sheets

(56) References Cited

U.S. PATENT DOCUMENTS

| | | |
|---|---|---|
| 4,201,224 A | 5/1980 | John |
| 4,279,258 A | 7/1981 | John |
| 4,411,273 A | 10/1983 | John |
| 4,417,592 A | 11/1983 | John |
| 4,537,198 A | 8/1985 | Corbett |
| 4,557,270 A | 12/1985 | John |
| 4,610,259 A | 9/1986 | Cohen et al. |
| 4,613,951 A | 9/1986 | Chu |
| 4,632,122 A | 12/1986 | Johansson et al. |
| 4,683,892 A | 8/1987 | Johansson et al. |
| 4,695,879 A | 9/1987 | Weinblatt |
| 4,736,751 A | 4/1988 | Gevins et al. |
| 4,800,888 A | 1/1989 | Itil et al. |
| 4,802,484 A | 2/1989 | Friedman et al. |
| 4,846,190 A | 7/1989 | John |
| 4,885,687 A | 12/1989 | Carey |
| 4,894,777 A | 1/1990 | Negishi et al. |
| 4,913,160 A | 4/1990 | John |
| 4,955,388 A | 9/1990 | Silberstein |
| 4,967,038 A | 10/1990 | Gevins et al. |
| 4,987,903 A | 1/1991 | Keppel et al. |
| 5,003,986 A | 4/1991 | Finitzo et al. |
| 5,010,891 A | 4/1991 | Chamoun |
| 5,038,782 A | 8/1991 | Gevins et al. |
| 5,052,401 A | 10/1991 | Sherwin |
| 5,083,571 A | 1/1992 | Prichep |
| RE34,015 E | 8/1992 | Duffy |
| 5,137,027 A | 8/1992 | Rosenfeld |
| 5,213,338 A | 5/1993 | Brotz |
| 5,226,177 A | 7/1993 | Nickerson |
| 5,243,517 A | 9/1993 | Schmidt et al. |
| 5,273,037 A | 12/1993 | Itil et al. |
| 5,291,888 A | 3/1994 | Tucker |
| 5,293,867 A | 3/1994 | Oommen |
| 5,295,491 A | 3/1994 | Gevins |
| 5,339,826 A | 8/1994 | Schmidt et al. |
| 5,357,957 A | 10/1994 | Itil et al. |
| 5,363,858 A | 11/1994 | Farwell |
| 5,392,788 A | 2/1995 | Hudspeth |
| 5,406,956 A | 4/1995 | Farwell |
| 5,447,166 A | 9/1995 | Gevins |
| 5,474,082 A | 12/1995 | Junker |
| 5,479,934 A | 1/1996 | Imran |
| 5,518,007 A | 5/1996 | Becker |
| 5,537,618 A | 7/1996 | Boulton et al. |
| 5,617,855 A | 4/1997 | Waletzky et al. |
| 5,655,534 A | 8/1997 | Ilmoniemi |
| 5,676,138 A | 10/1997 | Zawilinski |
| 5,720,619 A | 2/1998 | Fisslinger |
| 5,724,987 A | 3/1998 | Gevins et al. |
| 5,729,205 A | 3/1998 | Kwon |
| 5,740,035 A | 4/1998 | Cohen et al. |
| 5,762,611 A | 6/1998 | Lewis et al. |
| 5,771,897 A | 6/1998 | Zufrin |
| 5,787,187 A | 7/1998 | Bouchard et al. |
| 5,800,351 A | 9/1998 | Mann |
| 5,812,642 A | 9/1998 | Leroy |
| 5,817,029 A | 10/1998 | Gevins et al. |
| 5,848,399 A | 12/1998 | Burke |
| 5,945,863 A | 8/1999 | Coy |
| 5,961,332 A * | 10/1999 | Joao ............... 434/236 |
| 5,983,129 A | 11/1999 | Cowan et al. |
| 6,001,065 A | 12/1999 | DeVito |
| 6,021,346 A | 2/2000 | Ryu et al. |
| 6,052,619 A | 4/2000 | John |
| 6,099,319 A * | 8/2000 | Zaltman et al. ............. 434/236 |
| 6,120,440 A * | 9/2000 | Goknar ............ 600/300 |
| 6,128,521 A | 10/2000 | Marro et al. |
| 6,154,669 A | 11/2000 | Hunter et al. |
| 6,155,927 A | 12/2000 | Levasseur et al. |
| 6,161,030 A | 12/2000 | Levendowski et al. |
| 6,173,260 B1 | 1/2001 | Slaney |
| 6,175,753 B1 | 1/2001 | Menkes et al. |
| 6,228,038 B1 | 5/2001 | Claessens |
| 6,236,885 B1 | 5/2001 | Hunter et al. |
| 6,254,536 B1 | 7/2001 | DeVito |
| 6,280,198 B1 * | 8/2001 | Calhoun et al. .............. 434/236 |
| 6,286,005 B1 | 9/2001 | Cannon |
| 6,289,234 B1 | 9/2001 | Mueller |
| 6,292,688 B1 | 9/2001 | Patton |
| 6,301,493 B1 | 10/2001 | Marro et al. |
| 6,315,569 B1 | 11/2001 | Zaltman |
| 6,330,470 B1 | 12/2001 | Tucker et al. |
| 6,334,778 B1 * | 1/2002 | Brown ............ 434/258 |
| 6,374,143 B1 | 4/2002 | Berrang et al. |
| 6,381,481 B1 | 4/2002 | Levendowski et al. |
| 6,398,643 B1 | 6/2002 | Knowles et al. |
| 6,422,999 B1 | 7/2002 | Hill |
| 6,434,419 B1 | 8/2002 | Gevins et al. |
| 6,453,194 B1 | 9/2002 | Hill |
| 6,487,444 B2 | 11/2002 | Mimura |
| 6,488,617 B1 | 12/2002 | Katz |
| 6,510,340 B1 | 1/2003 | Jordan |
| 6,520,905 B1 | 2/2003 | Surve et al. |
| 6,545,685 B1 | 4/2003 | Dorbie |
| 6,575,902 B1 | 6/2003 | Burton |
| 6,577,329 B1 | 6/2003 | Flickner et al. |
| 6,585,521 B1 | 7/2003 | Obrador |
| 6,594,521 B2 | 7/2003 | Tucker |
| 6,598,006 B1 | 7/2003 | Honda et al. |
| 6,654,626 B2 | 11/2003 | Devlin et al. |
| 6,662,052 B1 | 12/2003 | Sarwal et al. |
| 6,665,560 B2 | 12/2003 | Becker et al. |
| 6,688,890 B2 | 2/2004 | von Buegner |
| 6,708,051 B1 | 3/2004 | Durousseau |
| 6,712,468 B1 | 3/2004 | Edwards |
| 6,754,524 B2 | 6/2004 | Johnson, Jr. |
| 6,757,556 B2 | 6/2004 | Gopenathan et al. |
| 6,788,882 B1 | 9/2004 | Geer et al. |
| 6,792,304 B1 | 9/2004 | Silberstein |
| 6,842,877 B2 * | 1/2005 | Robarts et al. .............. 715/708 |
| 6,904,408 B1 | 6/2005 | McCarthy et al. |
| 6,950,698 B2 | 9/2005 | Sarkela et al. |
| 6,958,710 B2 | 10/2005 | Zhang et al. |
| 6,973,342 B1 | 12/2005 | Swanson |
| 6,993,380 B1 | 1/2006 | Modarres |
| 7,120,880 B1 | 10/2006 | Dryer et al. |
| 7,130,673 B2 | 10/2006 | Tolvanen-Laakso et al. |
| 7,150,715 B2 | 12/2006 | Collura et al. |
| 7,164,967 B2 | 1/2007 | Etienne-Cummings et al. |
| 7,177,675 B2 | 2/2007 | Suffin et al. |
| 7,222,071 B2 | 5/2007 | Neuhauser et al. |
| 7,272,982 B2 | 9/2007 | Neuhauser et al. |
| 7,286,871 B2 | 10/2007 | Cohen |
| 7,340,060 B2 * | 3/2008 | Tomkins et al. .............. 380/277 |
| 7,391,835 B1 | 6/2008 | Gross et al. |
| 7,408,460 B2 | 8/2008 | Crystal et al. |
| 7,420,464 B2 | 9/2008 | Fitzgerald et al. |
| 7,443,292 B2 | 10/2008 | Jensen et al. |
| 7,460,827 B2 | 12/2008 | Schuster et al. |
| 7,463,143 B2 | 12/2008 | Forr et al. |
| 7,463,144 B2 | 12/2008 | Crystal et al. |
| 7,471,987 B2 | 12/2008 | Crystal et al. |
| 7,483,835 B2 | 1/2009 | Neuhauser et al. |
| 7,496,400 B2 | 2/2009 | Hoskonen et al. |
| 7,548,774 B2 | 6/2009 | Kurtz et al. |
| 7,551,952 B2 | 6/2009 | Gevins et al. |
| 7,592,908 B2 | 9/2009 | Zhang et al. |
| 7,614,066 B2 | 11/2009 | Urdang et al. |
| 7,623,823 B2 | 11/2009 | Zito et al. |
| 7,636,456 B2 | 12/2009 | Collins et al. |
| 7,650,793 B2 | 1/2010 | Jensen et al. |
| 7,689,272 B2 | 3/2010 | Farwell |
| 7,697,979 B2 | 4/2010 | Martinerie et al. |
| 7,698,238 B2 | 4/2010 | Barletta et al. |
| 7,720,351 B2 | 5/2010 | Levitan |
| 7,729,755 B2 | 6/2010 | Laken |
| 7,809,420 B2 | 10/2010 | Hannula et al. |
| 7,840,248 B2 | 11/2010 | Fuchs et al. |
| 7,840,250 B2 | 11/2010 | Tucker |
| 7,865,394 B1 | 1/2011 | Calloway |
| 7,892,764 B2 | 2/2011 | Xiong et al. |
| 7,908,133 B2 | 3/2011 | Neuhauser |
| 7,917,366 B1 | 3/2011 | Levanon et al. |

| Patent/Pub No. | Date | Inventor(s) |
|---|---|---|
| 7,962,315 B2 | 6/2011 | Jensen et al. |
| 7,988,557 B2 | 8/2011 | Soderlund |
| 8,014,847 B2 | 9/2011 | Shastri |
| 8,098,152 B2 | 1/2012 | Zhang et al. |
| 8,135,606 B2 | 3/2012 | Dupree |
| 8,151,298 B2 | 4/2012 | Begeja et al. |
| 8,165,916 B2 | 4/2012 | Hoffberg et al. |
| 8,209,224 B2 | 6/2012 | Pradeep et al. |
| 8,229,469 B2 | 7/2012 | Zhang et al. |
| 8,255,267 B2 | 8/2012 | Breiter |
| 8,270,814 B2 | 9/2012 | Pradeep et al. |
| 8,386,312 B2 | 2/2013 | Pradeep et al. |
| 8,386,313 B2 | 2/2013 | Pradeep et al. |
| 8,392,250 B2 | 3/2013 | Pradeep et al. |
| 8,392,251 B2 | 3/2013 | Pradeep et al. |
| 8,392,253 B2 | 3/2013 | Pradeep et al. |
| 8,392,254 B2 | 3/2013 | Pradeep et al. |
| 8,392,255 B2 | 3/2013 | Pradeep et al. |
| 8,396,744 B2 | 3/2013 | Pradeep et al. |
| 8,473,345 B2 | 6/2013 | Pradeep et al. |
| 8,484,081 B2 | 7/2013 | Pradeep et al. |
| 2001/0020236 A1 | 9/2001 | Cannon |
| 2001/0029468 A1 | 10/2001 | Yamaguchi et al. |
| 2001/0056225 A1 | 12/2001 | DeVito |
| 2002/0065826 A1 | 5/2002 | Bell et al. |
| 2002/0072952 A1 | 6/2002 | Hamzy et al. |
| 2002/0077534 A1 | 6/2002 | DuRousseau |
| 2002/0143627 A1 | 10/2002 | Barsade et al. |
| 2002/0155878 A1 | 10/2002 | Lert, Jr. et al. |
| 2002/0156842 A1 | 10/2002 | Signes et al. |
| 2002/0188216 A1 | 12/2002 | Kayyali et al. |
| 2002/0188217 A1 | 12/2002 | Farwell |
| 2002/0193670 A1 | 12/2002 | Garfield et al. |
| 2003/0013981 A1* | 1/2003 | Gevins et al. ............... 600/544 |
| 2003/0036955 A1 | 2/2003 | Tanaka et al. |
| 2003/0059750 A1* | 3/2003 | Bindler et al. ............... 434/236 |
| 2003/0073921 A1 | 4/2003 | Sohmer et al. |
| 2003/0100998 A2 | 5/2003 | Brunner et al. |
| 2003/0104865 A1 | 6/2003 | Itkis et al. |
| 2003/0165270 A1 | 9/2003 | Endrikhovski et al. |
| 2003/0177488 A1 | 9/2003 | Smith et al. |
| 2003/0233278 A1 | 12/2003 | Marshall |
| 2004/0005143 A1 | 1/2004 | Tsuru et al. |
| 2004/0013398 A1 | 1/2004 | Miura et al. |
| 2004/0015608 A1 | 1/2004 | Ellis et al. |
| 2004/0073129 A1 | 4/2004 | Caldwell et al. |
| 2004/0092809 A1 | 5/2004 | DeCharms |
| 2004/0098298 A1 | 5/2004 | Yin |
| 2004/0187167 A1 | 9/2004 | Maguire et al. |
| 2004/0210159 A1* | 10/2004 | Kibar ............... 600/558 |
| 2004/0220483 A1 | 11/2004 | Yeo et al. |
| 2004/0236623 A1 | 11/2004 | Gopalakrishnan |
| 2005/0010475 A1 | 1/2005 | Perkowski et al. |
| 2005/0076359 A1 | 4/2005 | Pierson et al. |
| 2005/0079474 A1 | 4/2005 | Lowe |
| 2005/0097594 A1 | 5/2005 | O'Donnell et al. |
| 2005/0107716 A1 | 5/2005 | Eaton et al. |
| 2005/0143629 A1 | 6/2005 | Farwell |
| 2005/0154290 A1 | 7/2005 | Langleben |
| 2005/0177058 A1 | 8/2005 | Sobell |
| 2005/0197590 A1 | 9/2005 | Osorio et al. |
| 2005/0203798 A1 | 9/2005 | Jensen et al. |
| 2005/0223237 A1 | 10/2005 | Barletta et al. |
| 2005/0227233 A1* | 10/2005 | Buxton et al. ............... 435/6 |
| 2005/0240956 A1 | 10/2005 | Smith et al. |
| 2005/0272017 A1 | 12/2005 | Neuhauser et al. |
| 2005/0273017 A1 | 12/2005 | Gordon |
| 2005/0273802 A1 | 12/2005 | Crystal et al. |
| 2005/0288954 A1 | 12/2005 | McCarthy et al. |
| 2005/0289582 A1 | 12/2005 | Tavares et al. |
| 2006/0003732 A1 | 1/2006 | Neuhauser et al. |
| 2006/0035707 A1 | 2/2006 | Nguyen et al. |
| 2006/0053110 A1 | 3/2006 | McDonald et al. |
| 2006/0093998 A1 | 5/2006 | Vertegaal |
| 2006/0111044 A1 | 5/2006 | Keller |
| 2006/0111644 A1 | 5/2006 | Guttag et al. |
| 2006/0129458 A1 | 6/2006 | Maggio |
| 2006/0167376 A1 | 7/2006 | Viirre et al. |
| 2006/0168613 A1 | 7/2006 | Wood et al. |
| 2006/0168630 A1 | 7/2006 | Davies |
| 2006/0256133 A1 | 11/2006 | Rosenberg |
| 2006/0257834 A1 | 11/2006 | Lee et al. |
| 2006/0259360 A1 | 11/2006 | Flinn et al. |
| 2006/0293921 A1 | 12/2006 | McCarthy et al. |
| 2007/0048707 A1 | 3/2007 | Caamano et al. |
| 2007/0055169 A1 | 3/2007 | Lee et al. |
| 2007/0060831 A1 | 3/2007 | Le et al. |
| 2007/0066874 A1 | 3/2007 | Cook |
| 2007/0066915 A1 | 3/2007 | Frei et al. |
| 2007/0066916 A1 | 3/2007 | Lemos |
| 2007/0067007 A1 | 3/2007 | Schulman et al. |
| 2007/0067305 A1 | 3/2007 | Ives |
| 2007/0078706 A1 | 4/2007 | Datta et al. |
| 2007/0079331 A1 | 4/2007 | Datta et al. |
| 2007/0106170 A1 | 5/2007 | Dunseath, Jr. et al. |
| 2007/0135727 A1 | 6/2007 | Virtanen et al. |
| 2007/0135728 A1 | 6/2007 | Snyder et al. |
| 2007/0225585 A1 | 9/2007 | Washbon et al. |
| 2007/0225674 A1 | 9/2007 | Molnar et al. |
| 2007/0226760 A1 | 9/2007 | Neuhauser et al. |
| 2007/0235716 A1 | 10/2007 | Delic et al. |
| 2007/0238945 A1 | 10/2007 | Delic et al. |
| 2007/0250846 A1 | 10/2007 | Swix et al. |
| 2007/0265507 A1 | 11/2007 | de Lemos |
| 2007/0294132 A1 | 12/2007 | Zhang et al. |
| 2007/0294705 A1 | 12/2007 | Gopalakrishnan |
| 2007/0294706 A1 | 12/2007 | Neuhauser et al. |
| 2008/0001600 A1 | 1/2008 | deCharms |
| 2008/0010110 A1 | 1/2008 | Neuhauser et al. |
| 2008/0027345 A1 | 1/2008 | Kumada et al. |
| 2008/0040740 A1 | 2/2008 | Plotnick et al. |
| 2008/0059997 A1 | 3/2008 | Plotnick et al. |
| 2008/0065468 A1 | 3/2008 | Berg et al. |
| 2008/0065721 A1 | 3/2008 | Cragun |
| 2008/0081961 A1 | 4/2008 | Westbrook et al. |
| 2008/0082019 A1 | 4/2008 | Ludving et al. |
| 2008/0086356 A1 | 4/2008 | Glassman et al. |
| 2008/0091512 A1 | 4/2008 | Marci et al. |
| 2008/0097854 A1 | 4/2008 | Young |
| 2008/0109840 A1 | 5/2008 | Walter et al. |
| 2008/0125110 A1 | 5/2008 | Ritter |
| 2008/0147488 A1 | 6/2008 | Tunick et al. |
| 2008/0152300 A1 | 6/2008 | Knee et al. |
| 2008/0204273 A1 | 8/2008 | Crystal et al. |
| 2008/0208072 A1 | 8/2008 | Fadem et al. |
| 2008/0214902 A1 | 9/2008 | Lee et al. |
| 2008/0221400 A1 | 9/2008 | Lee et al. |
| 2008/0221472 A1 | 9/2008 | Lee et al. |
| 2008/0221969 A1 | 9/2008 | Lee et al. |
| 2008/0222670 A1 | 9/2008 | Lee et al. |
| 2008/0222671 A1 | 9/2008 | Lee et al. |
| 2008/0228077 A1 | 9/2008 | Wilk et al. |
| 2008/0255949 A1 | 10/2008 | Genco et al. |
| 2008/0295126 A1 | 11/2008 | Lee et al. |
| 2009/0024049 A1 | 1/2009 | Pradeep et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0025023 A1 | 1/2009 | Pradeep et al. |
| 2009/0025024 A1 | 1/2009 | Beser et al. |
| 2009/0030287 A1 | 1/2009 | Pradeep et al. |
| 2009/0030303 A1 | 1/2009 | Pradeep et al. |
| 2009/0030717 A1 | 1/2009 | Pradeep et al. |
| 2009/0030762 A1 | 1/2009 | Lee et al. |
| 2009/0030930 A1 | 1/2009 | Pradeep et al. |
| 2009/0036755 A1 | 2/2009 | Pradeep et al. |
| 2009/0037575 A1 | 2/2009 | Crystal et al. |
| 2009/0062629 A1 | 3/2009 | Pradeep et al. |
| 2009/0062680 A1 | 3/2009 | Sandford |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0070798 A1 | 3/2009 | Lee et al. |
| 2009/0082643 A1 | 3/2009 | Pradeep et al. |
| 2009/0082689 A1 | 3/2009 | Guttag et al. |
| 2009/0083129 A1 | 3/2009 | Pradeep et al. |
| 2009/0088610 A1 | 4/2009 | Lee et al. |

| | | | |
|---|---|---|---|
| 2009/0112077 A1 | 4/2009 | Nguyen et al. |
| 2009/0253996 A1 | 10/2009 | Lee et al. |
| 2009/0327068 A1 | 12/2009 | Pradeep et al. |
| 2009/0328089 A1 | 12/2009 | Pradeep et al. |
| 2010/0004977 A1 | 1/2010 | Marci et al. |
| 2010/0022821 A1 | 1/2010 | Dubi et al. |
| 2010/0042012 A1 | 2/2010 | Alhussiny |
| 2010/0060300 A1 | 3/2010 | Mueller et al. |
| 2010/0125219 A1 | 5/2010 | Harris et al. |
| 2010/0145215 A1 | 6/2010 | Pradeep et al. |
| 2010/0145217 A1 | 6/2010 | Otto et al. |
| 2010/0180029 A1 | 7/2010 | Fourman |
| 2010/0183279 A1 | 7/2010 | Pradeep et al. |
| 2010/0186031 A1 | 7/2010 | Pradeep et al. |
| 2010/0186032 A1 | 7/2010 | Pradeep et al. |
| 2010/0198042 A1 | 8/2010 | Popescu et al. |
| 2010/0214318 A1 | 8/2010 | Pradeep et al. |
| 2010/0215289 A1 | 8/2010 | Pradeep et al. |
| 2010/0218208 A1 | 8/2010 | Holden |
| 2010/0249538 A1 | 9/2010 | Pradeep et al. |
| 2010/0249636 A1 | 9/2010 | Pradeep et al. |
| 2010/0250325 A1 | 9/2010 | Pradeep et al. |
| 2010/0257052 A1 | 10/2010 | Zito et al. |
| 2010/0325660 A1 | 12/2010 | Holden |
| 2011/0046473 A1 | 2/2011 | Pradeep et al. |
| 2011/0046502 A1 | 2/2011 | Pradeep et al. |
| 2011/0046503 A1 | 2/2011 | Pradeep et al. |
| 2011/0046504 A1 | 2/2011 | Pradeep et al. |
| 2011/0047121 A1 | 2/2011 | Pradeep et al. |
| 2011/0059422 A1 | 3/2011 | Masaoka |
| 2011/0105937 A1 | 5/2011 | Pradeep et al. |
| 2011/0106621 A1 | 5/2011 | Pradeep et al. |
| 2011/0106750 A1 | 5/2011 | Pradeep et al. |
| 2011/0119124 A1 | 5/2011 | Pradeep et al. |
| 2011/0119129 A1 | 5/2011 | Pradeep et al. |
| 2011/0208515 A1 | 8/2011 | Neuhauser |
| 2011/0237971 A1 | 9/2011 | Pradeep et al. |
| 2011/0248729 A2 | 10/2011 | Mueller et al. |
| 2011/0270620 A1 | 11/2011 | Pradeep et al. |
| 2011/0276504 A1 | 11/2011 | Pradeep et al. |
| 2011/0282231 A1 | 11/2011 | Pradeep et al. |
| 2011/0282232 A1 | 11/2011 | Pradeep et al. |
| 2011/0282749 A1 | 11/2011 | Pradeep et al. |
| 2012/0036004 A1 | 2/2012 | Pradeep et al. |
| 2012/0036005 A1 | 2/2012 | Pradeep et al. |
| 2012/0054018 A1 | 3/2012 | Pradeep et al. |
| 2012/0072289 A1 | 3/2012 | Pradeep et al. |
| 2012/0108995 A1 | 5/2012 | Pradeep et al. |
| 2012/0114305 A1 | 5/2012 | Holden |
| 2012/0130800 A1 | 5/2012 | Pradeep et al. |
| 2012/0245978 A1 | 9/2012 | Crystal et al. |
| 2013/0024272 A1 | 1/2013 | Pradeep et al. |

FOREIGN PATENT DOCUMENTS

| | | |
|---|---|---|
| WO | 95-18565 | 7/1995 |
| WO | 97/17774 | 5/1997 |
| WO | 97/40745 | 11/1997 |
| WO | 97/41673 | 11/1997 |
| WO | 02-100241 | 12/2002 |
| WO | 02-102238 | 12/2002 |
| WO | 2004/049225 | 6/2004 |
| WO | 2008-109694 | 9/2008 |
| WO | 2008-109699 | 9/2008 |
| WO | 2008/121651 | 10/2008 |
| WO | 2008-141340 | 10/2008 |
| WO | 2008/137579 | 11/2008 |
| WO | 2008-137581 | 11/2008 |
| WO | 2008/154410 | 12/2008 |
| WO | 2009/018374 | 2/2009 |
| WO | 2009/052833 | 4/2009 |

OTHER PUBLICATIONS

PCT Notification of Transmittal of the International Search Report and the Written Opinion of the International Searching Authority, or the Declaration, Application No. PCT/US 08/71639, dated Oct. 22, 2008.

ACNR, "Market Researchers Make Increasing Use of Brain Imaging," vol. 5, No. 3, Jul./Aug. 2005, 2 pages.

Sutherland, Max, "Neuromarketing: What's It All About?" From Max Sutherland's Weblog at www.sutherlandsurvey.com, Feb. 2007, p. 1-5.

Haq Amber, "This is Your Brain on Advertising," Business Week, Market Research, Oct. 8, 2007, 2 pages.

Barcelo, Francisco, et al., "Prefrontal Modulation of Visual Processing in Humans," Nature Neuroscience, vol. 3, No. 4, Apr. 2000, pp. 399-403.

Canolty, R.T., et al., "High Gamma Power Is Phase-Locked to Theta Oscillations in Human Neocortex," Science, vol. 313, Sep. 15, 2006, pp. 1626-1628.

Engel, Andreas, et al., "Dynamic Predictions: Oscillations and Synchrony in Top-Down Processing," Macmillan Magazines Ltd, vol. 2, Oct. 2001, pp. 704-716.

Fries, Pascal, "A Mechanism for Cognitive Dynamics: Neuronal Communication Through Neuronal Coherence," TRENDS in Cognitive Sciences, vol. 9, No. 10, Oct. 2005, p. 474-480.

Gazzaley, Adam, et al., "Top-down Enhancement and Suppression of the Magnitude and Speed of Neural Activity," Journal of Cognitive Neuroscience, vol. 17, No. 3, pp. 507-517.

Hartikainen, Kaisa, et al., "Emotionally Arousing Stimuli Compete with Attention to Left Hemispace," Editorial Manager(tm) for NeuroReport, Manuscipt Draft, Manuscript No. NR-D-07-5935R1, submitted Sep. 8, 2007, 26 pages.

Knight, Robert T., "Contribution of Human Hippocampal Region to Novelty Detection," Nature, vol. 383, Sep. 19, 1996, p. 256-259.

Knight Robert T., "Decreased Response to Novel Stimuli After Prefrontal Lesions in Man," Electroencephalography and Clinical Neurophysiology, vol. 59, 1984, pp. 9-20.

Miltner, Woflgang H.R., et al., "Coherence of Gamma-band EEG Activity as a Basis for Associative Learning," Nature, vol. 397, Feb. 4, 1999, pp. 434-436.

Final Rejection, issued by the United States Patent and Trademark Office in connection with U.S. Appl. No. 12/056,221, on Nov. 28, 2011, 44 pages.

Office Action, issued by the United States Patent and Trademark Office in connection with U.S. Appl. No. 12/113,863, on Dec. 22, 2011, 17 pages.

Office Action, issued by the United States Patent and Trademark Office in connection with U.S. Appl. No. 12/122,262, on Dec. 22, 2011, 17 pages.

Office Action, issued by the United States Patent and Trademark Office in connection with U.S. Appl. No. 12/135,074, on Dec. 22, 2011, 16 pages.

Office Action, issued by the United States Patent and Trademark Office in connection with U.S. Appl. No. 12/199,596, on Dec. 22, 2011, 15 pages.

Office Action, issued by the United States Patent and Trademark Office in connection with U.S. Appl. No. 12/200,813, on Dec. 22, 2011, 18 pages.

Extended European Search Report, issued by the European Patent Office in connection with European Application No. 11006934.1-2221, on Oct. 25, 2011, 5 pages.

Office Action, issued by the United States Patent and Trademark Office in connection with U.S. Appl. No. 12/199,583, on Dec. 29, 2011, 18 pages.

Final Rejection, issued by the United States Patent and Trademark Office in connection with U.S. Appl. No. 12/410,372, on Jan. 3, 2012, 10 pages.

Final Rejection, issued by the United States Patent and Trademark Office in connection with U.S. Appl. No. 12/413,297, on Jan. 4, 2012, 10 pages.

Office Action, issued by the United States Patent and Trademark Office in connection with U.S. Appl. No. 12/608,660, on Dec. 7, 2011, 43 pages.

Office Action, issued by the United States Patent and Trademark Office in connection with U.S. Appl. No. 12/199,557, on Dec. 22, 2011, 17 pages.

Office Action, issued by the United States Patent and Trademark Office in connection with U.S. Appl. No. 12/544,921, on Jan. 9, 2012, 13 pages.

Office Action, issued by the United States Patent and Trademark Office in connection with U.S. Appl. No. 12/357,302, on Jan. 17, 2012, 11 pages.
Final Rejection, issued by the United States Patent and Trademark Office in connection with U.S. Appl. No. 12/056,211, on Jul. 8, 2011, 16 pages.
Office Action, issued by the United States Patent and Trademark Office in connection with U.S. Appl. No. 12/056,211, on Jan. 7, 2011, 19 pages.
Office Action issued by the United States Patent and Trademark Office in connection with U.S. Appl. No. 12/056,221, on Apr. 15, 2011, 24 pages.
Final Rejection, issued by the United States Patent and Trademark Office in connection with U.S. Appl. No. 12/113,863, on Jun. 9, 2011, 12 pages.
Office Action, issued by the United States Patent and Trademark Office in connection with U.S. Appl. No. 12/113,863, on Dec. 27, 2010, 15 pages.
Final Rejection, issued by the United States Patent and Trademark Office in connection with U.S. Appl. No. 12/113,870, on Apr. 21, 2011, 10 pages.
Office Action, issued by the United States Patent and Trademark Office in connection with U.S. Appl. No. 12/113,870, on Dec. 3, 2010, 12 pages.
Office Action, issued by the United States Patent and Trademark Office in connection with U.S. Appl. No. 12/122,240, on Jun. 10, 2011, 12 pages.
Final Rejection, issued by the United States Patent and Trademark Office in connection with U.S. Appl. No. 12/122,262, on May 26, 2011, 15 pages.
Office Action, issued by the United States Patent and Trademark Office in connection with U.S. Appl. No. 12/122,262, on Dec. 9, 2010, 13 pages.
Final Rejection, issued by the United States Patent and Trademark Office in connection with U.S. Appl. No. 12/135,066, on Jan. 21, 2011, 16 pages.
Office Action, issued by the United States Patent and Trademark Office in connection with U.S. Appl. No. 12/135,066, on Oct. 28, 2010, 14 pages.
Notice of Panel Decision from Pre-Appeal Brief Review, issued by the United States Patent and Trademark Office in connection with U.S. Appl. No. 12/135,066, on May 31, 2011, 2 pages.
Office Action, issued by the United States Patent and Trademark Office in connection with U.S. Appl. No. 12/135,074, on Dec. 23, 2010, 14 pages.
Final Rejection, issued by the United States Patent and Trademark Office in connection with U.S. Appl. No. 12/135,074, on Jun. 9, 2011, 10 pages.
Office Action, issued by the United States Patent and Trademark Office in connection with U.S. Appl. No. 12/199,557, on Dec. 27, 2010, 14 pages.
Final Rejection, issued by the United States Patent and Trademark Office in connection with U.S. Appl. No. 12/199,557, on Jun. 9, 2011, 12 pages.
Final Rejection, issued by the United States Patent and Trademark Office in connection with U.S. Appl. No. 12/199,583, on Jun. 21, 2011, 14 pages.
Office Action, issued by the United States Patent and Trademark Office in connection with U.S. Appl. No. 12/199,583, on Dec. 27, 2010, 17 pages.
Final Rejection, issued by the United States Patent and Trademark Office in connection with U.S. Appl. No. 12/199,596, on Jun. 14, 2011, 13 pages.
Office Action, issued by the United States Patent and Trademark Office in connection with U.S. Appl. No. 12/199,596, on Dec. 27, 2010, 17 pages.
Final Rejection, issued by the United States Patent and Trademark Office in connection with U.S. Appl. No. 12/200,813, on Jul. 6, 2011, 13 pages.
Office Action, issued by the United States Patent and Trademark Office in connection with U.S. Appl. No. 12/200,813, on Dec. 27, 2010, 14 pages.
Office Action, issued by the United States Patent and Trademark Office in connection with U.S. Appl. No. 12/234,372, on Jun. 7, 2011, 10 pages.
Final Rejection, issued by the United States Patent and Trademark Office in connection with U.S. Appl. No. 12/135,069, on Feb. 17, 2011, 32 pages.
Office Action, issued by the United States Patent and Trademark Office in connection with U.S. Appl. No. 12/135,069, on Oct. 29, 2010, 21 pages.
Office Action, issued by the United States Patent and Trademark Office in connection with U.S. Appl. No. 12/357,315, on May 4, 2011, 9 pages.
Office Action, issued by the United States Patent and Trademark Office in connection with U.S. Appl. No. 12/410,380, on Jun. 7, 2011, 9 pages.
Office Action, issued by the United States Patent and Trademark Office in connection with U.S. Appl. No. 12/413,297, on Jul. 18, 2011, 9 pages.
Office Action, issued by the United States Patent and Trademark Office in connection with U.S. Appl. No. 12/608,685, on Jul. 12, 2011, 15 pages.
Office Action, issued by the United States Patent and Trademark Office in connection with U.S. Appl. No. 12/056,190, on Aug. 10, 2011, 28 pages.
Office Action, issued by the United States Patent and Trademark Office in connection with U.S. Appl. No. 12/357,322, on Aug. 23, 2011, 12 pages.
Office Action, issued by the United States Patent and Trademark Office in connection with U.S. Appl. No. 12/135,069, on Aug. 26, 2011, 33 pages.
Restriction Requirement, issued by the United States Patent and Trademark Office in connection with U.S. Appl. No. 12/122,253, on Sep. 2, 2011, 7 pages.
Office Action, issued by the United States Patent and Trademark Office in connection with U.S. Appl. No. 12/410,372, on Sep. 12, 2011, 12 pages.
Restriction Requirement, issued by the United States Patent and Trademark Office in connection with U.S. Appl. No. 12/182,851, on Sep. 12, 2011, 7 pages.
Office Action, issued by the United States Patent and Trademark Office in connection with U.S. Appl. No. 12/135,066, on Sep. 29, 2011, 37 pages.
Restriction Requirement, issued by the United States Patent and Trademark Office in connection with U.S. Appl. No. 12/056,225, on Oct. 3, 2011, 6 pages.
Office Action, issued by the United States Patent and Trademark Office in connection with U.S. Appl. No. 12/234,388, on Oct. 12, 2011, 27 pages.
Office Action, issued by the United States Patent and Trademark Office in connection with U.S. Appl. No. 12/234,372, on Oct. 13, 2011, 22 pages.
Office Action, issued by the United States Patent and Trademark Office in connection with U.S. Appl. No. 12/410,380, on Oct. 19, 2011, 21 pages.
Office Action, issued by the United States Patent and Trademark Office in connection with U.S. Appl. No. 12/357,315, on Oct. 26, 2011, 41 pages.
Office Action, issued by the United States Patent and Trademark Office in connection with U.S. Appl. No. 12/122,240, on Oct. 27, 2011, 39 pages.
International Preliminary Report on Patentability, issued by the International Bureau of WIPO in connection with International Application No. PCT/US08/058264, on Sep. 29, 2009, 1 page.
International Search Report, issued by the International Searching Authority in connection with International Application No. PCT/US08/058264, on Aug. 1, 2008, 2 pages.
Written Opinion, issued by the International Searching Authority in connection with International Application No. PCT/US08/058264, on Aug. 1, 2008, 5 pages.
International Preliminary Report on Patentability, issued by the International Bureau of WIPO in connection with International Application No. PCT/US08/062273, on Nov. 3, 2009, 1 page.

International Search Report, issued by the International Searching Authority in connection with International Application No. PCT/US08/062273, on Sep. 5, 2008, 2 pages.

Written Opinion, issued by the International Searching Authority in connection with International Application No. PCT/US08/062273, on Sep. 5, 2008, 4 pages.

International Preliminary Report on Patentability, issued by the International Bureau of WIPO in connection with International Application No. PCT/US08/062275, on Nov. 3, 2009, 1 page.

International Search Report, issued by the International Bureau in connection with International Application No. PCT/US08/062275, on Sep. 22, 2008, 2 pages.

Written Opinion, issued by the International Bureau in connection with International Application No. PCT/US08/062275, on Sep. 22, 2008, 6 pages.

International Preliminary Report on Patentability, issued by the International Bureau of WIPO in connection with International Application No. PCT/US08/063984, on Nov. 17, 2009, 1 page.

International Search Report, issued by the International Bureau in connection with International Application No. PCT/US08/063984, on Sep. 29, 2008, 3 pages.

Written Opinion, issued by the International Bureau in connection with International Application No. PCT/US08/063984, on Sep. 29, 2008, 4 pages.

International Preliminary Report on Patentability, issued by the International Bureau of WIPO in connection with International Application No. PCT/US08/063989, on Nov. 17, 2009, 1 page.

International Search Report, issued by the International Bureau in connection with International Application No. PCT/US08/063989, on Jul. 17, 2008, 2 pages.

Written Opinion, issued by the International Bureau in connection with International Application No. PCT/US08/063989, on Jul. 17, 2008, 4 pages.

International Preliminary Report on Patentability, issued by the International Bureau of WIPO in connection with International Application No. PCT/US08/066166, on Dec. 7, 2009, 1 page.

International Search Report, issued by the International Bureau in connection with International Application No. PCT/US08/066166, on Aug. 25, 2008, 2 pages.

Written Opinion, issued by the International Bureau in connection with International Application No. PCT/US08/066166, on Aug. 25, 2008, 6 pages.

International Preliminary Report on Patentability, issued by the International Bureau of WIPO in connection with International Application No. PCT/US08/071639, on Feb. 2, 2010, 1 page.

International Preliminary Report on Patentability, issued by the International Bureau of WIPO in connection with International Application No. PCT/US08/074467, on Mar. 2, 2010, 1 page.

International Search Report, issued by the International Bureau in connection with International Application No. PCT/US08/074467, on Nov. 17, 2008, 2 pages.

Written Opinion, issued by the International Bureau in connection with International Application No. PCT/US08/074467, on Nov. 17, 2008, 4 pages.

International Preliminary Report of Patentability, issued by the International Bureau in connection with International Application No. PCT/US10/021535, on Jul. 26, 2011, 1 page.

International Search Report, issued by the International Bureau in connection with International Application No. PCT/US10/021535, on Mar. 23, 2010, 3 pages.

Written Opinion, issued by the International Bureau in connection with International Application No. PCT/US10/021535, on Mar. 23, 2010, 4 pages.

International Preliminary Report of Patentability, issued by the International Bureau in connection with International Application No. PCT/US09/065368, on Jun. 23, 2011, 2 pages.

International Search Report, issued by the International Bureau in connection with International Application No. PCT/US09/065368, on Jan. 21, 2010, 3 pages.

Written Opinion, issued by the International Bureau in connection with International Application No. PCT/US09/065368, on Jan. 21, 2010, 7 pages.

Extended European Search Report, issued by the European Patent Office in connection with European Application No. 08744383.4-2221/2130146, on Jul. 27, 2011, 6 pages.

Extended European Search Report, issued by the European Patent Office in connection with European Application No. 10173095.0-2221, on Dec. 17, 2010, 3 pages.

Extended European Search Report, issued by the European Patent Office in connection with European Application No. 10189294.1-2221, on Mar. 21, 2011, 7 pages.

First Office Action, issued by the State Intellectual Property Office of P.R. China in connection with Patent Application No. 200880104982.1, on Jan. 25, 2011, 15 pages.

First Office Action, issued by the State Intellectual Property Office of P.R. China in connection with Patent Application No. 2008801015007, on May 25, 2011, 8 pages.

First Office Action, issued by the State Intellectual Property Office of P.R. China in connection with Patent Application No. 200880019166.0, on Jul. 22, 2011, 16 pages.

Decision of Rejection, issued by the State Intellectual Property Office of P.R. China in connection with Patent Application No. 200880104982.1, on Sep. 23, 2011, 10 pages.

Edgar, et al., "Digital Filters in ERP Research," in Event-Related Potentials: A Methods Handbook pp. 85-113, (Todd C. Handy, ed., 2005), 15 pages.

Simon-Thomas, et al, "Behavioral and Electrophysiological Evidence of a Right Hemisphere Bias for the Influence of Negative Emotion on Higher Cognition," Journal of Cognitive Neuroscience, pp. 518-529, Massachusetts Institute of Technology (2005), 12 pages.

Friedman, et al., "Event-Related Potential (ERP) Studies of Memory Encoding and Retrieval: A Selective Review," Microscopy Research and Technique 51:6-26, Wiley-Less, Inc. (2000), 23 pages.

Gaillard, "Problems and Paradigms in ERP Research," Biological Psychology, Elsevier Science Publisher B.V. (1988), 10 pages.

Hopf, et al., "Neural Sources of Focused Attention in Visual Search," Cerebral Cortex, 10:1233-1241, Oxford University Press, (Dec. 2000), 9 pages.

Swick, et al., "Contributions of Prefrontal Cortex to Recognition Memory: Electrophysiological and Behavioral Evidence," Neuropsychology, vol. 13, No. 2, pp. 155-170, American Psychological Association, Inc. (1999), 16 pages.

Luck, et al., "The sped of visual attention in schizophrenia: Electrophysiological and behavioral evidence," Schizophrenia Research, pp. 174-195, Elsevier B.V. www.sciencedirect.com, (2006), 22 pages.

Makeig, et al., "Mining event-related brain dynamics," TRENDS in Cognitive Sciences, vol. 8, No. 5, (May 2004), www.sciencedirect.com, 7 pages.

Herrmann, et al., "Mechanisms of human attention: event-related potentials and oscillations," Neuroscience and Biobehavioral Reviews, pp. 465-476, Elsevier Science Ltd., www.elsvevier.com/locate/neubiorev, (2001), 12 pages.

Paller, et al., "Validating neural correlates of familiarity," TRENDS in Cognitive Sciences, vol. 11, No. 6, www.sciencedirect.com, (May 2, 2007), 8 pages.

Picton, et al., "Guidelines for using human event-related potentials to study cognition: Recording standards and publication criteria," Psychophysiology, pp. 127-152, Society for Psychophysiological Research, (2000), 26 pages.

Yamaguchi, et al., "Rapid-Prefrontal—Hippocampal Habituation to Novel Events," The Journal of Neuroscience, pp. 5356-5363, Society for Neuroscience, (Apr. 29, 2004), 8 pages.

Rugg, et al., "Event-related potentials and recognition memory," TRENDS in Cognitive Sciences, vol. 11, No. 6, www.sciencedirect.com, (May 3, 2007), 7 pages.

Rugg, et al., "The ERP and cognitive psychology: conceptual issues," (Sep. 1996), 7 pages.

Spencer, "Averaging, Detection, and Classification of Single-Trial ERPs," in Event-Related Potentials: A Methods Handbook, pp. 209-227, (Todd C. Handy, ed., 2005), 10 pages.

Srinivasan, "High-Resolution EEG: Theory and Practice," in Event-Related Potentials: A Methods Handbook, pp. 167-188, (Todd C. Handy, ed., 2005), 12 pages.

Taheri, et al., "A dry electrode for EEG recording," Electroencephalography and clinical Neurophysiology, pp. 376-383, Elsevier Science Ireland Ltd. (1994), 8 pages.

Talsma, et al., "Methods for the Estimation and Removal of Artifacts and Overlap in ERP Waveforms," in Event-Related Potentials: A Methods Handbook, pp. 115-148, (Todd C. Handy, ed., 2005), 22 pages.

Davidson, et al., "The functional neuroanatomy of emotion and affective style," TRENDS in Cognitive Sciences, vol. 3, No. 1, (Jan. 1999), 11 pages.

Vogel, et al., "Electrophysiological Evidence for a Postperceptual Locus of Suppression During the Attentional Blink," Journal of Experimental Psychology: Human Perception and Performance, vol. 24, No. 6, pp. 1656-1674, (1998), 19 pages.

Rizzolatti et al., "The Mirror-Neuron System," Annu. Rev. Neurosci., vol. 27, pp. 169-192, (Mar. 5, 2004), 30 pages.

Woldorf, "Distortion of ERP averages due to overlap from temporally adjacent ERPs: Analysis and correction," Psychophysiology, Society for Psychophysiological Research, Cambridge University Press (1993), 22 pages.

Woodman, et al., "Serial Deployment of Attention During Visual Search," Journal of Experimental Psychology: Human Perception and Performance, vol. 29, No. 1, pp. 121-138, American Physiological Association (2003), 18 pages.

Knight, et al., "Prefrontal cortex regulates inhibition and excitation in distributed neural networks," Acta Psychologica vol. 101, pp. 159-178, Elsevier (1999), 20 pages.

Buschman, et al., "Top-Down versus Bottom-Up Control of Attention in the Prefrontal and posterior Parietal Cortices," Science, vol. 315, www.sciencemag.org/cgi/content/full/315/5820/1860, American Association for the Advancement of Science, (2007), 4 pages.

D'Esposito, "From cognitive to neural models of working memory," Phil. Trans. R. Soc. B, doi: 10.1098/rstb.2007.2086, (Mar. 30, 2007), 12 pages.

Dien, et al., "Application of Repeated Measures ANOVA to High-Dens Dataset: A Review and Tutorial," in Event-Related Potentials: A Methods Handbook pp. 57-82, (Todd C. Handy, ed., 2005), 14 pages.

Ambler, "Salience and Choice: Neural Correlates of Shopping Decisions," Psychology & Marketing, vol. 21, No. 4, p. 247-261, Wiley Periodicals, Inc., doi: 10.1002/mar20004, (Apr. 2004), 16 pages.

Hazlett, et al., "Emotional Response to Television Commercials: Facial EMG vs. Self-Report," Journal of Advertising Research, (Apr. 1999), 17 pages.

Makeig, et al., "Dynamic Brain Sources of Visual Evoked Responses," Science, vol. 295, www.sciencemag.org, (Jan. 25, 2002), 5 pages.

Aaker et al., "Warmth in Advertising: Measurement, Impact, and Sequence Effects," Journal of Consumer Research, vol. 12, No. 4, pp. 365-381, (Mar. 1986), 17 pages.

Belch et al., "Psychophysiological and cognitive Response to Sex in Advertising," Advances in Consumer Research, vol. 9, pp. 424-427, (1982), 6 pages.

Ruchkin et al., "Modality-specific processing streams in verbal working memory: evidence from spatio-temporal patterns of brain activity," Cognitive Brain Research, vol. 6, pp. 95-113, Elsevier, (1997), 19 pages.

Page et al., "Cognitive Neuroscience, Marketing and Research," Congress 2006—Foresight—The Predictive Power of Research Conference Papers, ESOMAR Publications, (Sep. 17, 2006), 25 pages.

Braeutigam, "Neuroeconomics—From neural systems to economic behavior," Brain Research Bulletin, vol. 67, pp. 355-360, Elsevier, (2005), 6 pages.

Lee et al., "What is 'neuromarketing'? A discussion and agenda for future research," International Journal of Psychophysiology, vol. 63, pp. 199-204, Elsevier (2006), 6 pages.

Crawford et al., "Self-generated happy and sad emotions in low and highly hypnotizable persons during waking and hypnosis: laterality and regional EEG activity differences," International Journal of Psychophysiology, vol. 24, pp. 239-266, (Dec. 1996), 28 pages.

Desmet, "Measuring Emotion: Development and Application of an Instrument to Measure Emotional Responses to Products," to be published in Funology: From Usability to Enjoyment, pp. 111-123, Kluwer Academic Publishers, (Blythe et al., eds., 2004), 13 pages.

Bagozzi et al., "The Role of Emotions in Marketing," Journal of the Academy of Marketing Science, vol. 27, No. 2, pp. 184-206, Academy of Marketing Science (1999), 23 pages.

Blakeslee, "If You Have a 'Buy Button' in Your Brain, What Pushes It?" The New York Times, www.nytimes.com, (Oct. 19, 2004), 3 pages.

Osborne, "Embedded Watermarking for image Verification in Telemedicine," Thesis submitted for the degree of Doctor of Philosophy, Electrical and Electronic Engineering, University of Adelaide (2005), 219 pages.

Nielsen, "Neuroinformatics in Functional Neuroimaging," Informatics and Mathematical Modeling, Technical University of Denmark, (Aug. 30, 2002), 241 pages.

Arousal in Sport, in Encyclopedia of Applied Psychology, vol. 1, p. 159, retrieved from Google Books, (Spielberger, ed., Elsevier Academic Press, 2004), 1 page.

Ziegenfuss, "Neuromarketing: Advertising Ethical & Medical Technology," The Brownstone Journal, vol. XII, Boston University, pp. 69-73, (May 2005), 5 pages.

Lekakos, "Personalized Advertising Services Through Hybrid Recommendation Methods: The Case of Digital Interactive Television," Department of Informatics, Cyprus University, (2004), 11 pages.

Ambler et al., "Ads on the Brain; A Neuro-Imaging Comparison of Cognitive and Affective Advertising Stimuli," London Business School, Centre for Marketing Working Paper, No. 00-902, (Mar. 2000), 23 pages.

U.S. Appl. No. 13/045,457, filed Mar. 10, 2011, (unpublished).
U.S. Appl. No. 12/778,810, filed May 12, 2010, (unpublished).
U.S. Appl. No. 12/778,828, filed May 12, 2010, (unpublished).
U.S. Appl. No. 13/104,821, filed May 10, 2011, (unpublished).
U.S. Appl. No. 13/104,840, filed May 10, 2011, (unpublished).
U.S. Appl. No. 12/853,197, filed Aug. 9, 2010, (unpublished).
U.S. Appl. No. 12/884,034, filed Sep. 16, 2010, (unpublished).
U.S. Appl. No. 12/868,531, filed Aug. 25, 2010, (unpublished).
U.S. Appl. No. 12/913,102, filed Oct. 27, 2010, (unpublished).
U.S. Appl. No. 12/853,213, filed Aug. 9, 2010, (unpublished).
U.S. Appl. No. 13/105,774, filed May 11, 2011, (unpublished).

Office Action, issued by the United States Patent and Trademark Office in connection with U.S. Appl. No. 12/868,531, on Mar. 1, 2012, 6 pages.

Office Action, issued by the United States Patent and Trademark Office in connection with U.S. Appl. No. 12/182,851, on Mar. 12, 2012, 14 pages.

Office Action, issued by the United States Patent and Trademark Office in connection with U.S. Appl. No. 12/608,685, on Mar. 29, 2012, 17 pages.

Office Action, issued by the United States Patent and Trademark Office in connection with U.S. Appl. No. 12/846,242, on Mar. 29, 2012, 15 pages.

Office Action, issued by the United States Patent and Trademark Office in connection with U.S. Appl. No. 12/234,388, on Apr. 6, 2012, 6 pages.

Office Action, issued by the United States Patent and Trademark Office in connection with U.S. Appl. No. 12/357,315, on Apr. 9, 2012, 17 pages.

Office Action, issued by the United States Patent and Trademark Office in connection with U.S. Appl. No. 12/544,958, on May 2, 2012, 14 pages.

English Translation of Office Action, issued by the Israel Patent Office in connection with Patent Application No. 203177, on Mar. 1, 2012, 2 pages.

Padgett et al., "Categorical Perception in Facial Emotion Classification," In Proceedings of the 18th Annual Conference of the Cognitive Science Society, pp. 249-253 (1996), 5 pages.

de Gelder et al., "Categorical Perception of Facial Expressions: Categories and their Internal Structure," Cognition and Emotion, vol. 11(1), pp. 1-23 (1997), 23 pages.

Bimler et al., "Categorical perception of facial expressions of emotion: Evidence from multidimensional scaling," Cognition and Emotion, vol. 15(5), pp. 633-658 (Sep. 2001), 26 pages.

Newell et al., "Categorical perception of familiar objects," Cognition, vol. 85, Issue 2, pp. 113-143 (Sep. 2002), 31 pages.

Meriam Webster Online Dictionary, Definition of Virtual Reality, available at http://www.meriam-webster.com/dictionary/virtual%20reality, 2 page.
Griss et al., "Characterization of micromachined spiked biopotential electrodes," Biomedical Engineering, IEEE Transactions (Jun. 2002), 8 pages.
"User monitoring," Sapien Systems, available at http://web.archive.org/web/20030818043339/http:/www.sapiensystems.com/eyetracking.html, (Aug. 18, 2003), 1 page.
Sullivan et al., "A brain-machine interface using dry-contact, low-noise EEG sensors," In Proceedings of the 2008 IEEE International Symposium on Circuits and Systems, (May 18, 2008), 4 pages.
Notice of Allowance, issued by the United States Patent and Trademark Office in connection with U.S. Appl. No. 12/357,302, on May 7, 2012, 16 pages.
Notice of Allowance, issued by the United States Patent and Trademark Office in connection with U.S. Appl. No. 12/868,531, on May 8, 2012, 16 pages.
Notice of Allowance, issued by the United States Patent and Trademark Office in connection with U.S. Appl. No. 12/608,696, on May 15, 2012, 16 pages.
Restriction Requirement, issued by the United States Patent and Trademark Office in connection with U.S. Appl. No. 12/545,455, on Jun. 13, 2012, 5 pages.
Office Action, issued by the United States Patent and Trademark Office in connection with U.S. Appl. No. 12/056,225, on Jun. 15, 2012, 9 pages.
Office Action, issued by the United States Patent and Trademark Office in connection with U.S. Appl. No. 12/544,934, on Jun. 18, 2012, 11 pages.
Office Action, issued by the United States Patent and Trademark Office in connection with U.S. Appl. No. 12/135,066, on Jun. 21, 2012, 9 pages.
Final Rejection, issued by the United States Patent and Trademark Office in connection with U.S. Appl. No. 12/608,660, on Jul. 10, 2012, 13 pages.
Second Office Action, issued by the State Intellectual Property Office of P.R. China in connection with Patent Application No. 200880019166.0, on Jun. 5, 2012, 8 pages.
Second Office Action, issued by the State Intellectual Property Office of P.R. China in connection with Patent Application No. 200880104982.1, on Jun. 29, 2012, 5 pages.
Barreto et al., "Physiologic Instrumentation for Real-time Monitoring of Affective State of Computer Users," WSEAS International Conference on Instrumentation, Measurement, Control, Circuits and Systems (IMCCAS), (2004), 6 pages.
Jung et al., "Analysis and Visualization of Single-Trial Event-Related Potentials," Human Brain Mapping vol. 14, 166-185 (2001), 20 pages.
Krugman, "Brain Wave Measures of Media Involvement," Journal of Advertising Research vol. 11, 3-9 (Feb. 1971), 7 pages.
The Mathworks, Inc., "MATLAB Data Analysis: Version 7," p. 4-19 (2005), 3 pages.
Klimesch, "EEG alpha and theta oscillations reflect cognitive and memory performance Jul. 20, 2012 a review and analysis," Brain Research Reviews, vol. 29, 169-195, (1999), 27 pages.
Krakow et al., "Methodology: EEG-correlated fMRI," Functional Imaging in the Epilepsies, (Lippincott Williams & Wilkins, 2000), 17 pages.
Allen et al., "A Method of Removing Imaging Artifact from Continuous EEG Recorded during Functional MRI," Neuroimage, vol. 12, 230-239, (Aug. 2000).
Examiner's Answer, issued by the United States Patent and Trademark Office in connection with U.S. Appl. No. 12/234,372, on May 23, 2012, 11 pages.
Advisory Action, issued by the United States Patent and Trademark Office in connection with U.S. Appl. No. 12/234,388, on Aug. 28, 2012, 3 pages.
Examiner's Answer, issued by the United States Patent and Trademark Office in connection with U.S. Appl. No. 12/410,380, on Jun. 8, 2012, 12 pages.

Examiner's Answer, issued by the United States Patent and Trademark Office in connection with U.S. Appl. No. 12/410,372, on Aug. 3, 2012, 8 pages.
Office Action, issued by the United States Patent and Trademark Office in connection with U.S. Appl. No. 12/545,455, on Aug. 29, 2012, 11 pages.
Final Rejection, issued by the United States Patent and Trademark Office in connection with U.S. Appl. No. 12/608,685, on Jul. 30, 2012, 15 pages.
Office Action, issued by the United States Patent and Trademark Office in connection with U.S. Appl. No. 12/778,810, on Aug. 31, 2012, 12 pages.
Office Action, issued by the United States Patent and Trademark Office in connection with U.S. Appl. No. 12/778,828, on Aug. 30, 2012, 9 pages.
Notice of Allowance, issued by the United States Patent and Trademark Office in connection with U.S. Appl. No. 12/056,190, on Sep. 17, 2012, 11 pages.
Notice of Allowance, issued by the United States Patent and Trademark Office in connection with U.S. Appl. No. 12/122,262, on Sep. 17, 2012, 11 pages.
Final Rejection, issued by the United States Patent and Trademark Office in connection with U.S. Appl. No. 12/122,253, on Sep. 17, 2012, 17 pages.
Examiner's Answer, issued by the United States Patent and Trademark Office in connection with U.S. Appl. No. 12/413,297, on Sep. 18, 2012, 18 pages.
Final Rejection, issued by the United States Patent and Trademark Office in connection with U.S. Appl. No. 12/546,586, on Sep. 18, 2012, 17 pages.
Notice of Allowance, issued by the United States Patent and Trademark Office in connection with U.S. Appl. No. 12/056,211, on Sep. 19, 2012, 10 pages.
Notice of Allowance, issued by the United States Patent and Trademark Office in connection with U.S. Appl. No. 12/135,074, on Sep. 19, 2012, 10 pages.
Notice of Allowance, issued by the United States Patent and Trademark Office in connection with U.S. Appl. No. 12/200,813, on Sep. 20, 2012, 11 pages.
Second Office Action, issued by the State Intellectual Property Office of China in connection with Chinese Patent Application No. 200880017883.X, on Aug. 10, 2012 (9 pages).
Oberman et al., "EEG evidence for mirror neuron activity during the observation of human and robot actions: Toward an analysis of the human qualities of interactive robots," Elsevier, Neurocomputing vol. 70 (2007), Jan. 2, 2007 (10 pages).
Notice of Allowance, issued by the United States Patent and Trademark Office in connection with U.S. Appl. No. 12/853,213, on Sep. 7, 2012, 9 pages.
Notice of Allowance, issued by the United States Patent and Trademark Office in connection with U.S. Appl. No. 12/199,583, on Sep. 26, 2012, 14 pages.
Notice of Allowance, issued by the United States Patent and Trademark Office in connection with U.S. Appl. No. 12/199,596, on Sep. 27, 2012, 14 pages.
Notice of Allowance, issued by the United States Patent and Trademark Office in connection with U.S. Appl. No. 12/199,557, on Sep. 28, 2012, 12 pages.
English Translation of Office Action, issued by the Israel Patent Office in connection with Patent Application No. 203177, on Sep. 27, 2012, 1 pages.
Notice of Allowance, issued by the United States Patent and Trademark Office in connection with U.S. Appl. No. 12/113,863, on Oct. 1, 2012, 12 pages.
Office Action, issued by the United States Patent and Trademark Office in connection with U.S. Appl. No. 13/444,149, on Oct. 4, 2012, 9 pages.
Final Office Action, issued by the United States Patent and Trademark Office in connection with U.S. Appl. No. 12/182,851, on Oct. 4, 2012, 14 pages.
Office Action, issued by the United States Patent and Trademark Office in connection with U.S. Appl. No. 12/234,388, on Oct. 5, 2012, 6 pages.

Office Action, issued by the Japanese Patent Office in connection with Patent Application No. 2010-501190, on Oct. 5, 2012, 5 pages.
Notice of Allowance, issued by the United States Patent and Trademark Office in connection with U.S. Appl. No. 12/853,197, on Oct. 16, 2012, 5 pages.
Notice of Allowance, issued by the United States Patent and Trademark Office in connection with U.S. Appl. No. 12/868,531, on Oct. 22, 2012, 5 pages.
English Translation of Office Action, issued by the Japanese Patent Office in connection with Patent Application No. 2010-506646, on Oct. 23, 2012, 3 pages.
Final Office Action, issued by the United States Patent and Trademark Office in connection with U.S. Appl. No. 12/846,242, on Nov. 29, 2012, 14 pages.
Clemons, "Resonance Marketing in the Age of the Truly Informed Consumer: Creating Profits through Differentiation and Delight," Wharton Information Strategy & Economics Blog 2, available at http://opim.wharton.upenn.edu/~clemons/blogs/resonanceblog.pdf, (Mar. 28, 2007), 8 pages.
English Translation of Office Action, issued by the Israel Patent Office in connection with Patent Application No. 203176, on Sep. 27, 2012, 1 pages.
Office Action, issued by the United States Patent and Trademark Office in connection with U.S. Appl. No. 12/056,211, on Feb. 16, 2012, 15 pages.
Final Rejection, issued by the United States Patent and Trademark Office in connection with U.S. Appl. No. 12/056,190, on Feb. 17, 2012, 22 pages.
Office Action, issued by the United States Patent and Trademark Office in connection with U.S. Appl. No. 12/122,253, on Feb. 17, 2012, 20 pages.
Mosby's Dictionary of Medicine, Nursing, & Health Professions, 2009, Mosby, Inc., Definition of Alpha Wave, 1 page.
Mosby's Dictionary of Medicine, Nursing, & Health Professions, 2009, Mosby, Inc., Definition of Beta Wave, 1 page.
U.S. Appl. No. 13/249,512, filed Sep. 30, 2011, (unpublished).
U.S. Appl. No. 13/249,525, filed Sep. 30, 2011, (unpublished).
U.S. Appl. No. 13/288,504, filed Nov. 3, 2011, (unpublished).
U.S. Appl. No. 13/288,571, filed Nov. 3, 2011, (unpublished).
U.S. Appl. No. 12/304,234, filed Nov. 3, 2011, (unpublished).
Office Action, issued by the United States Patent and Trademark Office in connection with U.S. Appl. No. 12/056,225, on Jan. 20, 2012, 12 pages.
Final Rejection, issued by the United States Patent and Trademark Office in connection with U.S. Appl. No. 12/135,066, on Jan. 24, 2012, 12 pages.
Office Action, issued by the United States Patent and Trademark Office in connection with U.S. Appl. No. 12/546,586, on Feb. 1, 2012, 17 pages.
Restriction Requirement, issued by the United States Patent and Trademark Office in connection with U.S. Appl. No. 12/544,958, on Feb. 10, 2012, 6 pages.
Final Rejection, issued by the United States Patent and Trademark Office in connection with U.S. Appl. No. 12/135,069, on Feb. 14, 2012, 35 pages.
Final Rejection, issued by the United States Patent and Trademark Office in connection with U.S. Appl. No. 12/357,322, on Feb. 14, 2012, 14 pages.
First Office Action, issued by the State Intellectual Property Office of P.R. China in connection with Patent Application No. 200880017883.X, on Nov. 30, 2011, 16 pages.
Meriam-Webster Online Dictionary definition for "tangible," available at http://www.meriam-webster.com/dictionary/tangible, 1 page.
English Translation of Office Action, issued by the Israel Patent Office in connection with Patent Application No. 203176, on Feb. 21, 2012, 2 pages.
Second Office Action, issued by the State Intellectual Property Office of P.R. China in connection with Patent Application No. 200880101500.7, on Apr. 5, 2012, 5 pages.
Notice of Allowance, issued by the United States Patent and Trademark Office in connection with U.S. Appl. No. 12/200,813, on Oct. 30, 2012, 5 pages.
Notice of Allowance, issued by the United States Patent and Trademark Office in connection with U.S. Appl. No. 12/056,190, on Nov. 2, 2012, 5 pages.
Restriction Requirement, issued by the United States Patent and Trademark Office in connection with U.S. Appl. No. 12/056,225, on Nov. 2, 2012, 5 pages.
Final Office Action, issued by the United States Patent and Trademark Office in connection with U.S. Appl. No. 12/135,066, on Nov. 13, 2012, 9 pages.
Notice of Allowance, issued by the United States Patent and Trademark Office in connection with U.S. Appl. No. 12/113,863, on Nov. 16, 2012, 5 pages.
Notice of Allowance, issued by the United States Patent and Trademark Office in connection with U.S. Appl. No. 12/056,211, on Nov. 21, 2012, 5 pages.
Notice of Allowance, issued by the United States Patent and Trademark Office in connection with U.S. Appl. No. 12/868,531, on Nov. 23, 2012, 5 pages.
Office Action, issued by the United States Patent and Trademark Office in connection with U.S. Appl. No. 12/913,102, on Dec. 7, 2012, 7 pages.
Final Office Action, issued by the United States Patent and Trademark Office in connection with U.S. Appl. No. 12/544,958, on Dec. 10, 2012, 16 pages.
Notice of Allowance, issued by the United States Patent and Trademark Office in connection with U.S. Appl. No. 12/853,197, on Dec. 20, 2012, 5 pages.
Notice of Allowance, issued by the United States Patent and Trademark Office in connection with U.S. Appl. No. 12/056,190, on Dec. 21, 2012, 14 pages.
Notice of Allowance, issued by the United States Patent and Trademark Office in connection with U.S. Appl. No. 12/056,211, on Dec. 21, 2012, 10 pages.
Notice of Allowance, issued by the United States Patent and Trademark Office in connection with U.S. Appl. No. 12/122,262, on Dec. 21, 2012, 19 pages.
Notice of Allowance, issued by the United States Patent and Trademark Office in connection with U.S. Appl. No. 12/135,074, on Dec. 21, 2012, 12 pages.
Notice of Allowance, issued by the United States Patent and Trademark Office in connection with U.S. Appl. No. 12/199,557, on Dec. 21, 2012, 14 pages.
Notice of Allowance, issued by the United States Patent and Trademark Office in connection with U.S. Appl. No. 12/199,596, on Dec. 21, 2012, 17 pages.
Notice of Allowance, issued by the United States Patent and Trademark Office in connection with U.S. Appl. No. 12/200,813, on Dec. 21, 2012, 9 pages.
Notice of Allowance, issued by the United States Patent and Trademark Office in connection with U.S. Appl. No. 12/853,213, on Dec. 21, 2012, 10 pages.
Notice of Allowance, issued by the United States Patent and Trademark Office in connection with U.S. Appl. No. 12/868,531, on Dec. 26, 2012, 2 pages.
Notice of Allowance, issued by the United States Patent and Trademark Office in connection with U.S. Appl. No. 12/113,863, on Dec. 31, 2012, 5 pages.
Notice of Allowance, issued by the United States Patent and Trademark Office in connection with U.S. Appl. No. 12/199,583, on Dec. 31, 2012, 10 pages.
Notice of Allowance, issued by the United States Patent and Trademark Office in connection with U.S. Appl. No. 12/199,583, on Jan. 11, 2013, 11 pages.
Final Office Action, issued by the United States Patent and Trademark Office in connection with U.S. Appl. No. 12/056,225, on Jan. 11, 2013, 11 pages.
Recertified IDS and Interview Summary, issued by the United States Patent and Trademark Office in connection with U.S. Appl. No. 12/853,197, on Jan. 16, 2013, 6 pages.
English Translation of Office Action, issued by the Israeli Patent Office in connection with Patent Application No. 201187, on Nov. 27, 2012, 2 pages.

Palva et al., "Phase Synchrony Among Neuronal Oscillations in the Human Cortex," Journal of Neuroscience 25 (2005), 3962-3972, 11 pages.
Lachaux et al., "Measuring Phase Synchrony in Brain Signals," Human Brain Mapping 8 (1999), 194-208, 15 pages.
English Translation of Third Office Action, issued by the State Intellectual Property Office of P.R. China in connection with Patent Application No. 200880101500.7, on Nov. 21 2012, 5 pages.
Extended European Search Report, issued by the European Patent Office in connection with European Application No. 08796890.5-2319/2170161, on Dec. 7, 2012, 9 pages.
Notice of Allowance, issued by the United States Patent and Trademark Office in connection with U.S. Appl. No. 12/199,557, on Jan. 29, 2013, 17 pages.
Notice of Allowance, issued by the United States Patent and Trademark Office in connection with U.S. Appl. No. 12/85,3197, on Jan. 29, 2013, 11 pages.
Notice of Allowance, issued by the United States Patent and Trademark Office in connection with U.S. Appl. No. 12/056,190, on Jan. 31, 2013, 5 pages.
Notice of Allowance, issued by the United States Patent and Trademark Office in connection with U.S. Appl. No. 12/113,863, on Jan. 31,2013, 5 pages.
Notice of Allowance, issued by the United States Patent and Trademark Office in connection with U.S. Appl. No. 12/135,074, on Jan. 31, 2013, 10 pages.
Notice of Allowance, issued by the United States Patent and Trademark Office in connection with U.S. Appl. No. 12/199,583, on Feb. 1, 2013, 11 pages.
Notice of Allowance, issued by the United States Patent and Trademark Office in connection with U.S. Appl. No. 12/200,813, on Feb. 1, 2013, 5 pages.
Notice of Allowance, issued by the United States Patent and Trademark Office in connection with U.S. Appl. No. 12/056,211, on Feb. 4, 2013, 5 pages.
Notice of Allowance, issued by the United States Patent and Trademark Office in connection with U.S. Appl. No. 12/122,262, on Feb. 5, 2013, 15 pages.
Notice of Allowance, issued by the United States Patent and Trademark Office in connection with U.S. Appl. No. 12/868,531, on Feb. 5, 2013, 8 pages.
Notice of Allowance, issued by the United States Patent and Trademark Office in connection with U.S. Appl. No. 12/853,213, on Feb. 5, 2013, 10 pages.
Notice of Allowance, issued by the United States Patent and Trademark Office in connection with U.S. Appl. No. 12/056,190, on Feb. 14, 2013, 5 pages.
Notice of Allowance, issued by the United States Patent and Trademark Office in connection with U.S. Appl. No. 12/234,388, on Feb. 15, 2013, 9 pages.
Notice of Allowance, issued by the United States Patent and Trademark Office in connection with U.S. Appl. No. 12/182,874, on Apr. 22, 2013, 11 pages.
Non-Final Office Action, issued by the United States Patent and Trademark Office in connection with U.S. Appl. No. 12/546,586, on Apr. 25, 2013, 34 pages.
Notification to Grant Patent Right for Invention, issued by the State Intellectual Property Office of P.R. China in connection with Patent Application No. 200880104982.1, on Jan. 14, 2013, 4 pages.
Extended European Search Report, issued by the European Patent Office in connection with European Application No. 08770372.4-1265/2152155, on Feb. 6, 2013, 7 pages.
English Translation of Third Office Action, issued by the State Intellectual Property Office of P.R. China in connection with Patent Application No. 200880017883.X, on Mar. 18, 2013, 8 pages.
Notification to Grant Patent Right for Invention, issued by the State Intellectual Property Office of P.R. China in connection with Patent Application No. 200880101500.7, on Apr. 3, 2013, 2 pages.
Non-Final Office Action, issued by the United States Patent and Trademark Office in connection with U.S. Appl. No. 13/444,149, on May 2, 2013, 27 pages.
Notice of Allowance, issued by the United States Patent and Trademark Office in connection with U.S. Appl. No. 12/056,190, on May 8, 2013, 4 pages.
Notice of Allowance, issued by the United States Patent and Trademark Office in connection with U.S. Appl. No. 12/056,211, on May 8, 2013, 5 pages.
Notice of Allowance, issued by the United States Patent and Trademark Office in connection with U.S. Appl. No. 12/135,074, on May 8, 2013, 5 pages.
Notice of Allowance, issued by the United States Patent and Trademark Office in connection with U.S. Appl. No. 12/199,596, on May 8, 2013, 7 pages.
Notice of Allowance, issued by the United States Patent and Trademark Office in connection with U.S. Appl. No. 13/569,711, on May 14, 2013, 6 pages.
Office Communication to Applicant, issued by the United States Patent and Trademark Office in connection with U.S. Appl. No. 12/234,388, on May 24, 2013, 2 pages.
Non-Final Office Action, issued by the United States Patent and Trademark Office in connection with U.S. Appl. No. 12/884,034, on May 28, 2013, 12 pages.
Notice of Allowance, issued by the United States Patent and Trademark Office in connection with U.S. Appl. No. 12/135,074, on May 31, 2013, 5 pages.
Notice of Allowance, issued by the United States Patent and Trademark Office in connection with U.S. Appl. No. 12/056,211, on Jun. 3, 2013, 5 pages.
Notice of Allowance, issued by the United States Patent and Trademark Office in connection with U.S. Appl. No. 12/199,596, on Jun. 3, 2013, 5 pages.
Notice of Allowance, issued by the United States Patent and Trademark Office in connection with U.S. Appl. No. 12/199,596, on Jun. 11, 2013, 7 pages.
Notice of Allowance, issued by the United States Patent and Trademark Office in connection with U.S. Appl. No. 12/545,455, on Jun. 11, 2013, 9 pages.
Notice of Allowance, issued by the United States Patent and Trademark Office in connection with U.S. Appl. No. 12/056,190, on Jun. 13, 2013, 5 pages.
Office Communication to Applicant, issued by the United States Patent and Trademark Office in connection with U.S. Appl. No. 12/234,388, on Jun. 13, 2013, 2 pages.
Notice of Allowance, issued by the United States Patent and Trademark Office in connection with U.S. Appl. No. 12/135,074, on Jun. 21, 2013, 5 pages.
Non-Final Office Action, issued by the United States Patent and Trademark Office in connection with U.S. Appl. No. 13/105,774, on Jun. 26, 2013, 10 pages.
Merriam-Webster Online Dictionary, Definition for "Resonance," available at http://www.merriam-webster.com/dictionary/resonance, 4 pages.
Enghoff, Sigurd, Thesis: "Moving ICA and Time-Frequency Analysis in Event-Related EEG Studies of Selective Attention," Technical University of Denmark, (Dec. 1999), 54 pages.
Zhang, P., "Will You Use Animation on Your Web Pages?" Doing Business on the Internet: Opportunities and Pitfalls, C. Romm and F. Sudweeks (eds.), Spring-Verlag (1999), 17 pages.
English Translation of Office Action, issued by the Israeli Patent Office in connection with Patent Application No. 203176, on Apr. 23, 2013, 1 page.

* cited by examiner

| Stimulus Attributes Data Model 201 | | | | |
|---|---|---|---|---|
| Channel 203 | Media 205 | Time Span 207 | Audience 209 | Demography 211 | ... |

| Stimulus Purpose Data Model 215 | | |
|---|---|---|
| Intent 217 | Objectives 219 | Entity Temporal And Spatial Information 221 | ... |

| Stimulus Attributes Data Model 221 | | | |
|---|---|---|---|
| Creation Attributes 223 | Ownership Attributes 225 | Broadcast Attributes 227 | Statistical, Demographic, And Survey Based Identifiers 229 | ... |

Figure 2

| Dataset Data Model 301 | | | | |
|---|---|---|---|---|
| Experiment Name 303 | Client Attributes 305 | Subject Pool 307 | Logistics Information 309 | Stimulus Material 311 | ... |

| Subject Attributes Data Model 315 | | |
|---|---|---|
| Subject Name 317 | Demographic Attributes 319 | Contact Information 321 | ... |

| Neuro-Feedback Association Data Model 325 | | |
|---|---|---|
| Experiment Protocols 327 | Modalities included 329 | Experiment Design Parameters 333 | ... |

| Data Collection Data Model 337 | | | |
|---|---|---|---|
| Recording Attributes 339 | Equipment Attributes 341 | Modalities Recorded 343 | Data Storage Attributes 345 | ... |

| Preset Query Data Model 349 | | | |
|---|---|---|---|
| Query Name 351 | Accessed Data Collection 353 | Access Security Attributes 355 | Refresh Attributes 357 | ... |

Figure 3

| Subject Attributes Queries 415 | | |
|---|---|---|
| Location 417 | Demographic Attributes 419 | Session Information 421 | ... |

| Experimental Design Queries 425 | | |
|---|---|---|
| Experiment Protocols 427 | Product Category 429 | Surveys Included 431 | Stimulus Used 433 | ... |

| Response Assessment Queries 437 | | |
|---|---|---|
| Attention Score 439 | Emotion Score 441 | Retention Score 443 | Effectiveness Score 445 | ... |

Figure 4

| Client Assessment Summary Reports 501 | | |
|---|---|---|
| Effectiveness 503 | Component Assessment 505 | Resonance Measures 507 | ... |

| Client Cumulative Reports 511 | | |
|---|---|---|
| Media Grouped 513 | Campaign Grouped 515 | Time/Location Grouped 517 | ... |

| Industry Cumulative And Syndicated Reports 521 | | | |
|---|---|---|---|
| Aggregate Assessment 523 | Top Performers 525 | Bottom Performers 527 | Outliers 529 | Trend 531 | ... |

Figure 5

NEURO-RESPONSE STIMULUS AND STIMULUS ATTRIBUTE RESONANCE ESTIMATOR

CROSS REFERENCE TO RELATED APPLICATIONS

This patent claims priority to Provisional Patent Application Ser. No. 60/952,723, titled Neuro-Physiological And Neuro-Behavioral Stimulus And Stimulus Attribute Resonance Estimator, by Anantha Pradeep, Robert T. Knight, and Ramachandran Gurumoorthy, and filed on Jul. 30, 2007. This patent is related to U.S. patent application Ser. Nos. 12/056,190; 12/056,211; 12/056,221; 12/056,225; 12/113,863; 12/113,870; 12/122,240; 12/122,253; 12/122,262; 12/135,066; 12/135,074; 12/182,851; 12/199,557; 12/199,583; 12/199,596; 12/200,813; 12/234,372; 12/135,069; 12/234,388; 12/544,921; 12/544,934; 12/546,586; 12/544,958; 12/846,242; 12/410,380; 12/410,372; 12/413,297; 12/545,455; 12/608,660; 12/608,685; 13/444,149; 12/608,696; 12/731,868; 13/045,457; 12/778,810; 12/778,828; 13/104,821; 13/104,840; 12/853,197; 12/884,034; 12/868,531; 12/913,102; 12/853,213; and 13/105,774.

TECHNICAL FIELD

The present disclosure relates to a stimulus and stimulus attribute resonance estimator.

DESCRIPTION OF RELATED ART

Conventional systems for estimating stimulus and stimulus attribute resonance are limited. Some audience resonance measurement systems are based on demographic information, statistical data, and survey based response collection. However, conventional systems are subject to semantic, syntactic, metaphorical, cultural, and interpretive errors.

Consequently, it is desirable to provide improved methods and apparatus for estimating stimulus and stimulus attribute resonance.

BRIEF DESCRIPTION OF THE DRAWINGS

The disclosure may best be understood by reference to the following description taken in conjunction with the accompanying drawings, which illustrate particular example embodiments.

FIG. 2 illustrates examples of stimulus attributes that can be included in a stimulus attributes repository.

FIG. 3 illustrates examples of data models that can be used with a stimulus and response repository.

FIG. 4 illustrates one example of a query that can be used with the resonance estimation system.

FIG. 5 illustrates one example of a report generated using the resonance estimation system.

DESCRIPTION OF PARTICULAR EMBODIMENTS

Figure 1:
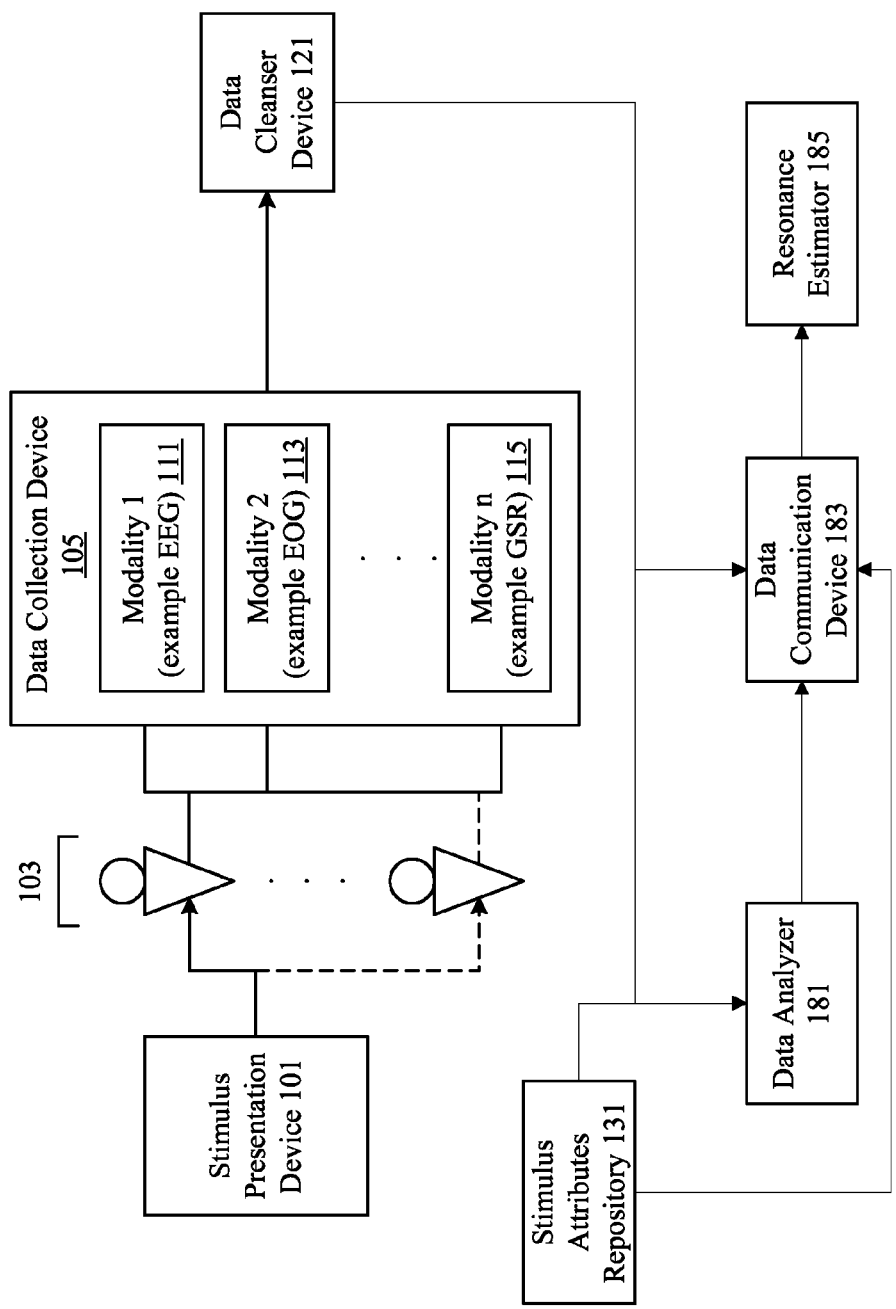
FIG. 1 illustrates one example of a system for estimating stimulus and stimulus attribute resonance.

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

For example, the techniques and mechanisms of the present invention will be described in the context of particular types of data such as central nervous system, autonomic nervous system, and effector data. However, it should be noted that the techniques and mechanisms of the present invention apply to a variety of different types of data. It should be noted that various mechanisms and techniques can be applied to any type of stimuli. In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise. For example, a system uses a processor in a variety of contexts. However, it will be appreciated that a system can use multiple processors while remaining within the scope of the present invention unless otherwise noted. Furthermore, the techniques and mechanisms of the present invention will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory. Consequently, a connection does not necessarily mean a direct, unimpeded connection unless otherwise noted.

Overview

A system determines neuro-response stimulus and stimulus attribute resonance. Stimulus material and stimulus material attributes such as communication, concept, experience, message, images, audio, pricing, and packaging are evaluated using neuro-response data collected with mechanisms such as Event Related Potential (ERP), Electroencephalography (EEG), Galvanic Skin Response (GSR), Electrocardiograms (EKG), Electrooculography (EOG), eye tracking, and facial emotion encoding. Neuro-response data is analyzed to determine stimulus and stimulus attribute resonance.

Example Embodiments

Stimulus and stimulus attribute resonance estimators have been in use for years. Typically, stimulus and stimulus attribute resonance estimators are based on audience resonance measurement systems that typically rely on demographic information, statistical information, and survey based response collection. One problem with conventional stimulus and stimulus attribute resonance estimators is that conventional resonance estimators do not measure the inherent message resonance that is attributable to the stimulus. They are also prone to semantic, syntactic, metaphorical, cultural, and interpretive errors thereby preventing the accurate and repeatable targeting of the audience.

Conventional systems do not use neuro-behavioral and neuro-physiological response blended manifestations in assessing the user response and do not elicit an individual customized neuro-physiological and/or neuro-behavioral response to the stimulus.

Conventional devices also fail to blend multiple datasets, and blended manifestations of multi-modal responses, across multiple datasets, individuals and modalities, to reveal and validate the elicited measures of preference and resonance to stimulus and stimulus attributes In these respects, the neuro-physiological and neuro-behavioral stimulus and stimulus attribute resonance estimator according to the present invention substantially departs from the conventional concepts and designs of the prior art, and in so doing provides an apparatus primarily developed for the purpose of providing a method and a system for the neuro-physiological and neuro-behavioral response based measurement of audience response and resonance to attributes of marketing, advertising and other audio/visual/tactile/olfactory stimulus including but not limited to communication, concept, experience, message, images, audio, pricing, packaging.

The techniques and mechanisms of the present invention use neuro-response measurements such as central nervous system, autonomic nervous system, and effector measurements to improve resonance estimation. Some examples of central nervous system measurement mechanisms include Functional Magnetic Resonance Imaging (fMRI) and Electroencephalography (EEG). fMRI measures blood oxygenation in the brain that correlates with increased neural activity. However, current implementations of fMRI have poor temporal resolution of few seconds. EEG measures electrical activity associated with post synaptic currents occurring in the milliseconds range. Subcranial EEG can measure electrical activity with the most accuracy, as the bone and dermal layers weaken transmission of a wide range of frequencies. Nonetheless, surface EEG provides a wealth of electrophysiological information if analyzed properly. Even portable EEG with dry electrodes provide a large amount of neuro-response information.

Autonomic nervous system measurement mechanisms include Galvanic Skin Response (GSR), Electrocardiograms (EKG), pupillary dilation, etc. Effector measurement mechanisms include Electrooculography (EOG), eye tracking, facial emotion encoding, reaction time etc.

According to various embodiments, the techniques and mechanisms of the present invention intelligently blend multiple modes and manifestations of precognitive neural signatures with cognitive neural signatures and post cognitive neurophysiological manifestations to more accurately perform resonance estimation. In some examples, autonomic nervous system measures are themselves used to validate central nervous system measures. Effector and behavior responses are blended and combined with other measures. According to various embodiments, central nervous system, autonomic nervous system, and effector system measurements are aggregated into a measurement that allows determination of stimulus and stimulus attribute resonance.

In particular embodiments, subjects are exposed to stimulus material and data such as central nervous system, autonomic nervous system, and effector data is collected during exposure. According to various embodiments, data is collected in order to determine a resonance measure that aggregates multiple component measures that assess resonance data. In particular embodiments, specific event related potential (ERP) analyses and/or event related power spectral perturbations (ERPSPs) are evaluated for different regions of the brain both before a subject is exposed to stimulus and each time after the subject is exposed to stimulus.

Pre-stimulus and post-stimulus differential as well as target and distracter differential measurements of ERP time domain components at multiple regions of the brain are determined (DERP). Event related time-frequency analysis of the differential response to assess the attention, emotion and memory retention (DERPSPs) across multiple frequency bands including but not limited to theta, alpha, beta, gamma and high gamma is performed. In particular embodiments, single trial and/or averaged DERP and/or DERPSPs can be used to enhance the resonance measure A resonance estimate may also incorporate relationship assessments using brain regional coherence measures of segments of the stimuli relevant to the entity/relationship, segment effectiveness measures synthesizing the attention, emotional engagement and memory retention estimates based on the neuro-physiological measures including time-frequency analysis of EEG measurements, and differential saccade related neural signatures during segments where coupling/relationship patterns are emerging in comparison to segments with non-coupled interactions.

According to various embodiments, a resonance estimator can include automated systems with or without human intervention for the elicitation of potential object/individual groupings. For example, these could also include pattern recognition and object identification techniques. These sub-systems could include a hardware implementation and/or software implementations.

A variety of stimulus materials such as entertainment and marketing materials, media streams, billboards, print advertisements, text streams, music, performances, sensory experiences, etc. can be analyzed. According to various embodiments, enhanced neuro-response data is generated using a data analyzer that performs both intra-modality measurement enhancements and cross-modality measurement enhancements. According to various embodiments, brain activity is measured not just to determine the regions of activity, but to determine interactions and types of interactions between various regions. The techniques and mechanisms of the present invention recognize that interactions between neural regions support orchestrated and organized behavior. Attention, emotion, memory, and other abilities are not merely based on one part of the brain but instead rely on network interactions between brain regions.

The techniques and mechanisms of the present invention further recognize that different frequency bands used for multi-regional communication can be indicative of the effectiveness of stimuli. In particular embodiments, evaluations are calibrated to each subject and synchronized across subjects. In particular embodiments, templates are created for subjects to create a baseline for measuring pre and post stimulus differentials. According to various embodiments, stimulus generators are intelligent and adaptively modify specific parameters such as exposure length and duration for each subject being analyzed.

A variety of modalities can be used including EEG, GSR, EKG, pupillary dilation, EOG, eye tracking, facial emotion encoding, reaction time, etc. Individual modalities such as EEG are enhanced by intelligently recognizing neural region communication pathways. Cross modality analysis is enhanced using a synthesis and analytical blending of central nervous system, autonomic nervous system, and effector signatures. Synthesis and analysis by mechanisms such as time and phase shifting, correlating, and validating intra-modal determinations allow generation of a composite output characterizing the significance of various data responses to effectively perform resonance estimation.

FIG. 1 illustrates one example of a system for performing resonance estimation using central nervous system, autonomic nervous system, and/or effector measures. According to various embodiments, the resonance estimation system includes a stimulus presentation device 101. In particular embodiments, the stimulus presentation device 101 is merely a display, monitor, screen, etc., that displays stimulus material to a user. The stimulus material may be a media clip, a commercial, pages of text, a brand image, a performance, a magazine advertisement, a movie, an audio presentation, and may even involve particular tastes, smells, textures and/or sounds. The stimuli can involve a variety of senses and occur with or without human supervision. Continuous and discrete modes are supported. According to various embodiments, the stimulus presentation device 101 also has protocol generation capability to allow intelligent customization of stimuli provided to multiple subjects in different markets.

According to various embodiments, stimulus presentation device 101 could include devices such as televisions, cable consoles, computers and monitors, projection systems, display devices, speakers, tactile surfaces, etc., for presenting the stimuli including but not limited to advertising and entertainment from different networks, local networks, cable channels, syndicated sources, websites, internet content aggregators, portals, service providers, etc.

According to various embodiments, the subjects are connected to data collection devices 105. The data collection devices 105 may include a variety of neuro-response measurement mechanisms including neurological and neurophysiological measurements systems such as EEG, EOG, GSR, EKG, pupillary dilation, eye tracking, facial emotion encoding, and reaction time devices, etc. According to various embodiments, neuro-response data includes central nervous system, autonomic nervous system, and effector data. In particular embodiments, the data collection devices 105 include EEG 111, EOG 113, and GSR 115. In some instances, only a single data collection device is used. Data collection may proceed with or without human supervision.

The data collection device 105 collects neuro-response data from multiple sources. This includes a combination of devices such as central nervous system sources (EEG), autonomic nervous system sources (GSR, EKG, pupillary dilation), and effector sources (EOG, eye tracking, facial emotion encoding, reaction time). In particular embodiments, data collected is digitally sampled and stored for later analysis. In particular embodiments, the data collected could be analyzed in real-time. According to particular embodiments, the digital sampling rates are adaptively chosen based on the neurophysiological and neurological data being measured.

In one particular embodiment, the resonance estimation system includes EEG 111 measurements made using scalp level electrodes, EOG 113 measurements made using shielded electrodes to track eye data, GSR 115 measurements performed using a differential measurement system, a facial muscular measurement through shielded electrodes placed at specific locations on the face, and a facial affect graphic and video analyzer adaptively derived for each individual.

In particular embodiments, the data collection devices are clock synchronized with a stimulus presentation device 101. In particular embodiments, the data collection devices 105 also include a condition evaluation subsystem that provides auto triggers, alerts and status monitoring and visualization components that continuously monitor the status of the subject, data being collected, and the data collection instruments. The condition evaluation subsystem may also present visual alerts and automatically trigger remedial actions. According to various embodiments, the data collection devices include mechanisms for not only monitoring subject neuro-response to stimulus materials, but also include mechanisms for identifying and monitoring the stimulus materials. For example, data collection devices 105 may be synchronized with a set-top box to monitor channel changes. In other examples, data collection devices 105 may be directionally synchronized to monitor when a subject is no longer paying attention to stimulus material. In still other examples, the data collection devices 105 may receive and store stimulus material generally being viewed by the subject, whether the stimulus is a program, a commercial, printed material, or a scene outside a window. The data collected allows analysis of neuro-response information and correlation of the information to actual stimulus material and not mere subject distractions.

According to various embodiments, the resonance estimation system also includes a data cleanser device 121. In particular embodiments, the data cleanser device 121 filters the collected data to remove noise, artifacts, and other irrelevant data using fixed and adaptive filtering, weighted averaging, advanced component extraction (like PCA, ICA), vector and component separation methods, etc. This device cleanses the data by removing both exogenous noise (where the source is outside the physiology of the subject, e.g. a phone ringing while a subject is viewing a video) and endogenous artifacts (where the source could be neurophysiological, e.g. muscle movements, eye blinks, etc.).

The artifact removal subsystem includes mechanisms to selectively isolate and review the response data and identify epochs with time domain and/or frequency domain attributes that correspond to artifacts such as line frequency, eye blinks, and muscle movements. The artifact removal subsystem then cleanses the artifacts by either omitting these epochs, or by replacing these epoch data with an estimate based on the other clean data (for example, an EEG nearest neighbor weighted averaging approach).

According to various embodiments, the data cleanser device 121 is implemented using hardware, firmware, and/or software. It should be noted that although a data cleanser device 121 is shown located after a data collection device 105 and before data analyzer 181, the data cleanser device 121 like other components may have a location and functionality that varies based on system implementation. For example, some systems may not use any automated data cleanser device whatsoever while in other systems, data cleanser devices may be integrated into individual data collection devices.

According to various embodiments, an optional stimulus attributes repository 131 provides information on the stimulus material being presented to the multiple subjects. According to various embodiments, stimulus attributes include properties of the stimulus materials as well as purposes, presentation attributes, report generation attributes, etc. In particular embodiments, stimulus attributes include time span, channel, rating, media, type, etc. Stimulus attributes may also include positions of entities in various frames, object relationships, locations of objects and duration of display. Purpose attributes include aspiration and objects of the stimulus including excitement, memory retention, associations, etc. Presentation attributes include audio, video, imagery, and messages needed for enhancement or avoidance. Other attributes may or may not also be included in the stimulus attributes repository or some other repository.

The data cleanser device 121 and the stimulus attributes repository 131 pass data to the data analyzer 181. The data analyzer 181 uses a variety of mechanisms to analyze underlying data in the system to determine resonance. According to various embodiments, the data analyzer customizes and extracts the independent neurological and neuro-physiological parameters for each individual in each modality, and blends the estimates within a modality as well as across modalities to elicit an enhanced response to the presented stimulus material. In particular embodiments, the data analyzer 181 aggregates the response measures across subjects in a dataset.

According to various embodiments, neurological and neuro-physiological signatures are measured using time domain analyses and frequency domain analyses. Such analyses use parameters that are common across individuals as well as parameters that are unique to each individual. The analyses could also include statistical parameter extraction and fuzzy logic based attribute estimation from both the time and frequency components of the synthesized response.

In some examples, statistical parameters used in a blended effectiveness estimate include evaluations of skew, peaks, first and second moments, population distribution, as well as fuzzy estimates of attention, emotional engagement and memory retention responses.

According to various embodiments, the data analyzer 181 may include an intra-modality response synthesizer and a cross-modality response synthesizer. In particular embodiments, the intra-modality response synthesizer is configured to customize and extract the independent neurological and neurophysiological parameters for each individual in each modality and blend the estimates within a modality analytically to elicit an enhanced response to the presented stimuli. In particular embodiments, the intra-modality response synthesizer also aggregates data from different subjects in a dataset.

According to various embodiments, the cross-modality response synthesizer or fusion device blends different intra-modality responses, including raw signals and signals output. The combination of signals enhances the measures of effectiveness within a modality. The cross-modality response fusion device can also aggregate data from different subjects in a dataset.

According to various embodiments, the data analyzer 181 also includes a composite enhanced effectiveness estimator (CEEE) that combines the enhanced responses and estimates from each modality to provide a blended estimate of the effectiveness. In particular embodiments, blended estimates are provided for each exposure of a subject to stimulus materials. The blended estimates are evaluated over time to assess resonance characteristics. According to various embodiments, numerical values are assigned to each blended estimate. The numerical values may correspond to the intensity of neuro-response measurements, the significance of peaks, the change between peaks, etc. Higher numerical values may correspond to higher significance in neuro-response intensity. Lower numerical values may correspond to lower significance or even insignificant neuro-response activity. In other examples, multiple values are assigned to each blended estimate. In still other examples, blended estimates of neuro-response significance are graphically represented to show changes after repeated exposure.

According to various embodiments, the data analyzer 181 provides analyzed and enhanced response data to a data communication device 183. It should be noted that in particular instances, a data communication device 183 is not necessary. According to various embodiments, the data communication device 183 provides raw and/or analyzed data and insights. In particular embodiments, the data communication device 183 may include mechanisms for the compression and encryption of data for secure storage and communication.

According to various embodiments, the data communication device 183 transmits data using protocols such as the File Transfer Protocol (FTP), Hypertext Transfer Protocol (HTTP) along with a variety of conventional, bus, wired network, wireless network, satellite, and proprietary communication protocols. The data transmitted can include the data in its entirety, excerpts of data, converted data, and/or elicited response measures. According to various embodiments, the data communication device is a set top box, wireless device, computer system, etc. that transmits data obtained from a data collection device to a resonance estimator 185. In particular embodiments, the data communication device may transmit data even before data cleansing or data analysis. In other examples, the data communication device may transmit data after data cleansing and analysis.

In particular embodiments, the data communication device 183 sends data to a resonance estimator 185. According to various embodiments, the resonance estimator 185 assesses and extracts resonance patterns. In particular embodiments, the resonance estimator 185 determines entity positions in various stimulus segments and matches position information with eye tracking paths while correlating saccades with neural assessments of attention, memory retention, and emotional engagement. In particular embodiments, the resonance estimator 185 also collects and integrates user behavioral and survey responses with the analyzed response data to more effectively estimate resonance.

A variety of data can be stored for later analysis, management, manipulation, and retrieval. In particular embodiments, the repository could be used for tracking stimulus attributes and presentation attributes, audience responses and optionally could also be used to integrate audience measurement information.

As with a variety of the components in the system, the resonance estimator can be co-located with the rest of the system and the user, or could be implemented in a remote location. It could also be optionally separated into an assessment repository system that could be centralized or distributed at the provider or providers of the stimulus material. In other examples, the resonance estimator is housed at the facilities of a third party service provider accessible by stimulus material providers and/or users.

FIG. 2 illustrates examples of data models that may be provided with a stimulus attributes repository. According to various embodiments, a stimulus attributes data model 201 includes a channel 203, media type 205, time span 207, audience 209, and demographic information 211. A stimulus purpose data model 215 may include intents 217 and objectives 219. According to various embodiments, stimulus attributes data model 201 also includes spatial and temporal information 221 about entities and emerging relationships between entities.

According to various embodiments, another stimulus attributes data model 221 includes creation attributes 223, ownership attributes 225, broadcast attributes 227, and statistical, demographic and/or survey based identifiers for automatically integrating the neuro-physiological and neuro-behavioral response with other attributes and meta-information associated with the stimulus.

FIG. 3 illustrates examples of data models that can be used for storage of information associated with tracking and measurement of resonance. According to various embodiments, a dataset data model 301 includes an experiment name 303 and/or identifier, client attributes 305, a subject pool 307, logistics information 309 such as the location, date, and time of testing, and stimulus material 311 including stimulus material attributes.

In particular embodiments, a subject attribute data model 315 includes a subject name 317 and/or identifier, contact information 321, and demographic attributes 319 that may be useful for review of neurological and neuro-physiological data. Some examples of pertinent demographic attributes include marriage status, employment status, occupation, household income, household size and composition, ethnicity, geographic location, sex, race. Other fields that may be included in data model 315 include shopping preferences, entertainment preferences, and financial preferences. Shopping preferences include favorite stores, shopping frequency, categories shopped, favorite brands. Entertainment preferences include network/cable/satellite access capabilities, favorite shows, favorite genres, and favorite actors. Financial preferences include favorite insurance companies, preferred investment practices, banking preferences, and favorite online financial instruments. A variety of subject attributes may be included in a subject attributes data model 315 and data models may be preset or custom generated to suit particular purposes.

According to various embodiments, data models for neuro-feedback association 325 identify experimental protocols 327, modalities included 329 such as EEG, EOG, GSR, surveys conducted, and experiment design parameters 333 such as segments and segment attributes. Other fields may include experiment presentation scripts, segment length, segment details like stimulus material used, inter-subject variations, intra-subject variations, instructions, presentation order, survey questions used, etc. Other data models may include a data collection data model 337. According to various embodiments, the data collection data model 337 includes recording attributes 339 such as station and location identifiers, the data and time of recording, and operator details. In particular embodiments, equipment attributes 341 include an amplifier identifier and a sensor identifier.

Modalities recorded 343 may include modality specific attributes like EEG cap layout, active channels, sampling frequency, and filters used. EOG specific attributes include the number and type of sensors used, location of sensors applied, etc. Eye tracking specific attributes include the type of tracker used, data recording frequency, data being recorded, recording format, etc. According to various embodiments, data storage attributes 345 include file storage conventions (format, naming convention, dating convention), storage location, archival attributes, expiry attributes, etc.

A preset query data model 349 includes a query name 351 and/or identifier, an accessed data collection 353 such as data segments involved (models, databases/cubes, tables, etc.), access security attributes 355 included who has what type of access, and refresh attributes 357 such as the expiry of the query, refresh frequency, etc. Other fields such as push-pull preferences can also be included to identify an auto push reporting driver or a user driven report retrieval system.

FIG. 4 illustrates examples of queries that can be performed to obtain data associated with resonance estimation. According to various embodiments, queries are defined from general or customized scripting languages and constructs, visual mechanisms, a library of preset queries, diagnostic querying including drill-down diagnostics, and eliciting what if scenarios. According to various embodiments, subject attributes queries 415 may be configured to obtain data from a neuro-informatics repository using a location 417 or geographic information, session information 421 such as testing times and dates, and demographic attributes 419. Demographics attributes include household income, household size and status, education level, age of kids, etc.

Other queries may retrieve stimulus material based on shopping preferences of subject participants, countenance, physiological assessment, completion status. For example, a user may query for data associated with product categories, products shopped, shops frequented, subject eye correction status, color blindness, subject state, signal strength of measured responses, alpha frequency band ringers, muscle movement assessments, segments completed, etc. Experimental design based queries may obtain data from a neuro-informatics repository based on experiment protocols 427, product category 429, surveys included 431, and stimulus provided 433. Other fields that may used include the number of protocol repetitions used, combination of protocols used, and usage configuration of surveys.

Client and industry based queries may obtain data based on the types of industries included in testing, specific categories tested, client companies involved, and brands being tested. Response assessment based queries 437 may include attention scores 439, emotion scores, 441, retention scores 443, and effectiveness scores 445. Such queries may obtain materials that elicited particular scores.

Response measure profile based queries may use mean measure thresholds, variance measures, number of peaks detected, etc. Group response queries may include group statistics like mean, variance, kurtosis, p-value, etc., group size, and outlier assessment measures. Still other queries may involve testing attributes like test location, time period, test repetition count, test station, and test operator fields. A variety of types and combinations of types of queries can be used to efficiently extract data.

FIG. 5 illustrates examples of reports that can be generated. According to various embodiments, client assessment summary reports 501 include effectiveness measures 503, component assessment measures 505, and resonance measures 507. Effectiveness assessment measures include composite assessment measure(s), industry/category/client specific placement (percentile, ranking, etc.), actionable grouping assessment such as removing material, modifying segments, or fine tuning specific elements, etc, and the evolution of the effectiveness profile over time. In particular embodiments, component assessment reports include component assessment measures like attention, emotional engagement scores, percentile placement, ranking, etc. Component profile measures include time based evolution of the component measures and profile statistical assessments. According to various embodiments, reports include the number of times material is assessed, attributes of the multiple presentations used, evolution of the response assessment measures over the multiple presentations, and usage recommendations.

According to various embodiments, client cumulative reports 511 include media grouped reporting 513 of all stimulus assessed, campaign grouped reporting 515 of stimulus assessed, and time/location grouped reporting 517 of stimulus assessed. According to various embodiments, industry cumulative and syndicated reports 521 include aggregate assessment responses measures 523, top performer lists 525, bottom performer lists 527, outliers 529, and trend reporting 531. In particular embodiments, tracking and reporting includes specific products, categories, companies, brands.

Figure 6:
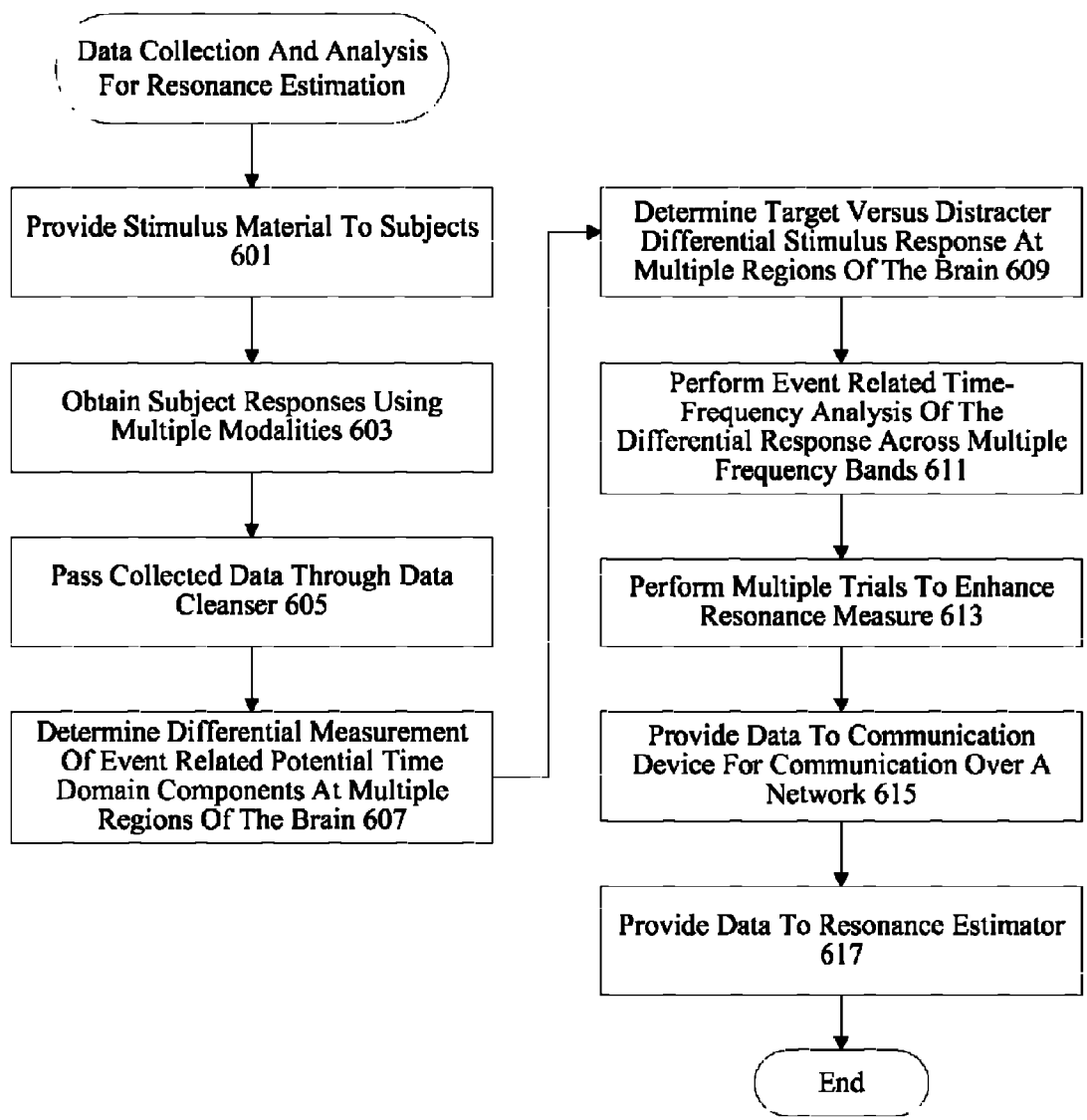
FIG. 6 illustrates one example of a technique for performing data analysis.

FIG. 6 illustrates one example of resonance estimation. At 601, stimulus material is provided to multiple subjects in multiple geographic markets. According to various embodiments, stimulus includes streaming video and audio provided over mechanisms such as broadcast television, cable television, satellite, etc. The stimulus may be presented to users in different geographic markets at the same or varying times. In particular embodiments, subjects view stimulus in their own homes in group or individual settings. At 603, subject responses are collected using a variety of modalities, such as EEG, ERP, EOG, GSR, etc. In some examples, verbal and written responses can also be collected and correlated with neurological and neurophysiological responses. At 605, data is passed through a data cleanser to remove noise and artifacts that may make data more difficult to interpret. According to various embodiments, the data cleanser removes EEG electrical activity associated with blinking and other endogenous/exogenous artifacts.

According to various embodiments, data analysis is performed. Data analysis may include intra-modality response synthesis and cross-modality response synthesis to enhance effectiveness measures. It should be noted that in some particular instances, one type of synthesis may be performed without performing other types of synthesis. For example, cross-modality response synthesis may be performed with or without intra-modality synthesis.

A variety of mechanisms can be used to perform data analysis. In particular embodiments, a stimulus attributes repository 131 is accessed to obtain attributes and characteristics of the stimulus materials, along with purposes, intents, objectives, etc. In particular embodiments, EEG response data is synthesized to provide an enhanced assessment of effectiveness. According to various embodiments, EEG measures electrical activity resulting from thousands of simultaneous neural processes associated with different portions of the brain. EEG data can be classified in various bands. According to various embodiments, brainwave frequencies include delta, theta, alpha, beta, and gamma frequency ranges. Delta waves are classified as those less than 4 Hz and are prominent during deep sleep. Theta waves have frequencies between 3.5 to 7.5 Hz and are associated with memories, attention, emotions, and sensations. Theta waves are typically prominent during states of internal focus.

Alpha frequencies reside between 7.5 and 13 Hz and typically peak around 10 Hz. Alpha waves are prominent during states of relaxation. Beta waves have a frequency range between 14 and 30 Hz. Beta waves are prominent during states of motor control, long range synchronization between brain areas, analytical problem solving, judgment, and decision making. Gamma waves occur between 30 and 60 Hz and are involved in binding of different populations of neurons together into a network for the purpose of carrying out a certain cognitive or motor function, as well as in attention and memory. Because the skull and dermal layers attenuate waves in this frequency range, brain waves above 75-80 Hz are difficult to detect and are often not used for stimuli response assessment.

However, the techniques and mechanisms of the present invention recognize that analyzing high gamma band (kappa-band: Above 60 Hz) measurements, in addition to theta, alpha, beta, and low gamma band measurements, enhances neurological attention, emotional engagement and retention component estimates. In particular embodiments, EEG measurements including difficult to detect high gamma or kappa band measurements are obtained, enhanced, and evaluated. Subject and task specific signature sub-bands in the theta, alpha, beta, gamma and kappa bands are identified to provide enhanced response estimates. According to various embodiments, high gamma waves (kappa-band) above 80 Hz (typically detectable with sub-cranial EEG and/or magnetoencephalograophy) can be used in inverse model-based enhancement of the frequency responses to the stimuli.

Various embodiments of the present invention recognize that particular sub-bands within each frequency range have particular prominence during certain activities. A subset of the frequencies in a particular band is referred to herein as a sub-band. For example, a sub-band may include the 40-45 Hz range within the gamma band. In particular embodiments, multiple sub-bands within the different bands are selected while remaining frequencies are band pass filtered. In particular embodiments, multiple sub-band responses may be enhanced, while the remaining frequency responses may be attenuated.

An information theory based band-weighting model is used for adaptive extraction of selective dataset specific, subject specific, task specific bands to enhance the effectiveness measure. Adaptive extraction may be performed using fuzzy scaling. Stimuli can be presented and enhanced measurements determined multiple times to determine the variation profiles across multiple presentations. Determining various profiles provides an enhanced assessment of the primary responses as well as the longevity (wear-out) of the marketing and entertainment stimuli. The synchronous response of multiple individuals to stimuli presented in concert is measured to determine an enhanced across subject synchrony measure of effectiveness. According to various embodiments, the synchronous response may be determined for multiple subjects residing in separate locations or for multiple subjects residing in the same location.

Although a variety of synthesis mechanisms are described, it should be recognized that any number of mechanisms can be applied—in sequence or in parallel with or without interaction between the mechanisms.

Although intra-modality synthesis mechanisms provide enhanced significance data, additional cross-modality synthesis mechanisms can also be applied. A variety of mechanisms such as EEG, Eye Tracking, GSR, EOG, and facial emotion encoding are connected to a cross-modality synthesis mechanism. Other mechanisms as well as variations and enhancements on existing mechanisms may also be included. According to various embodiments, data from a specific modality can be enhanced using data from one or more other modalities. In particular embodiments, EEG typically makes frequency measurements in different bands like alpha, beta and gamma to provide estimates of significance. However, the techniques of the present invention recognize that significance measures can be enhanced further using information from other modalities.

For example, facial emotion encoding measures can be used to enhance the valence of the EEG emotional engagement measure. EOG and eye tracking saccadic measures of object entities can be used to enhance the EEG estimates of significance including but not limited to attention, emotional engagement, and memory retention. According to various embodiments, a cross-modality synthesis mechanism performs time and phase shifting of data to allow data from different modalities to align. In some examples, it is recognized that an EEG response will often occur hundreds of milliseconds before a facial emotion measurement changes. Correlations can be drawn and time and phase shifts made on an individual as well as a group basis. In other examples, saccadic eye movements may be determined as occurring before and after particular EEG responses. According to various embodiments, time corrected GSR measures are used to scale and enhance the EEG estimates of significance including attention, emotional engagement and memory retention measures.

Evidence of the occurrence or non-occurrence of specific time domain difference event-related potential components (like the DERP) in specific regions correlates with subject responsiveness to specific stimulus. According to various embodiments, ERP measures are enhanced using EEG time-frequency measures (ERPSP) in response to the presentation of the marketing and entertainment stimuli. Specific portions are extracted and isolated to identify ERP, DERP and ERPSP analyses to perform. In particular embodiments, an EEG frequency estimation of attention, emotion and memory retention (ERPSP) is used as a co-factor in enhancing the ERP, DERP and time-domain response analysis.

EOG measures saccades to determine the presence of attention to specific objects of stimulus. Eye tracking measures the subject's gaze path, location and dwell on specific objects of stimulus. According to various embodiments, EOG and eye tracking is enhanced by measuring the presence of lambda waves (a neurophysiological index of saccade effectiveness) in the ongoing EEG in the occipital and extra striate regions, triggered by the slope of saccade-onset to estimate the significance of the EOG and eye tracking measures. In particular embodiments, specific EEG signatures of activity such as slow potential shifts and measures of coherence in time-frequency responses at the Frontal Eye Field (FEF) regions that preceded saccade-onset are measured to enhance the effectiveness of the saccadic activity data.

GSR typically measures the change in general arousal in response to stimulus presented. According to various embodiments, GSR is enhanced by correlating EEG/ERP responses and the GSR measurement to get an enhanced estimate of subject engagement. The GSR latency baselines are used in constructing a time-corrected GSR response to the stimulus. The time-corrected GSR response is co-factored with the EEG measures to enhance GSR significance measures.

According to various embodiments, facial emotion encoding uses templates generated by measuring facial muscle positions and movements of individuals expressing various emotions prior to the testing session. These individual specific facial emotion encoding templates are matched with the individual responses to identify subject emotional response. In particular embodiments, these facial emotion encoding measurements are enhanced by evaluating inter-hemispherical asymmetries in EEG responses in specific frequency bands and measuring frequency band interactions. The techniques of the present invention recognize that not only are particular frequency bands significant in EEG responses, but particular frequency bands used for communication between particular areas of the brain are significant. Consequently, these EEG responses enhance the EMG, graphic and video based facial emotion identification.

According to various embodiments, post-stimulus versus pre-stimulus differential measurements of ERP time domain components in multiple regions of the brain (DERP) are measured at 607. The differential measures give a mechanism for eliciting responses attributable to the stimulus. For example the messaging response attributable to an ad or the brand response attributable to multiple brands is determined using pre-resonance and post-resonance estimates At 609, target versus distracter stimulus differential responses are determined for different regions of the brain (DERP). At 611, event related time-frequency analysis of the differential response (DERPSPs) are used to assess the attention, emotion and memory retention measures across multiple frequency bands. According to various embodiments, the multiple frequency bands include theta, alpha, beta, gamma and high gamma or kappa. At 613, multiple trials are performed to enhance resonance measures.

At 615, processed data is provided to a data communication device for transmission over a network such as a wireless, wireline, satellite, or other type of communication network capable of transmitting data. Data is provided to resonance estimator at 617. According to various embodiments, the data communication device transmits data using protocols such as the File Transfer Protocol (FTP), Hypertext Transfer Protocol (HTTP) along with a variety of conventional, bus, wired network, wireless network, satellite, and proprietary communication protocols. The data transmitted can include the data in its entirety, excerpts of data, converted data, and/or elicited response measures. According to various embodiments, data is sent using a telecommunications, wireless, Internet, satellite, or any other communication mechanisms that is capable of conveying information from multiple subject locations for data integration and analysis. The mechanism may be integrated in a set top box, computer system, receiver, mobile device, etc.

In particular embodiments, the data communication device sends data to the resonance estimator. According to various embodiments, the resonance estimator combines analyzed and enhanced responses to the stimulus material while using information about stimulus material attributes such as the location, movement, acceleration, and spatial relationships of various entities and objects. In particular embodiments, the resonance estimator also collects and integrates user behavioral and survey responses with the analyzed and enhanced response data to more effectively assessment resonance patterns.

Figure 7:
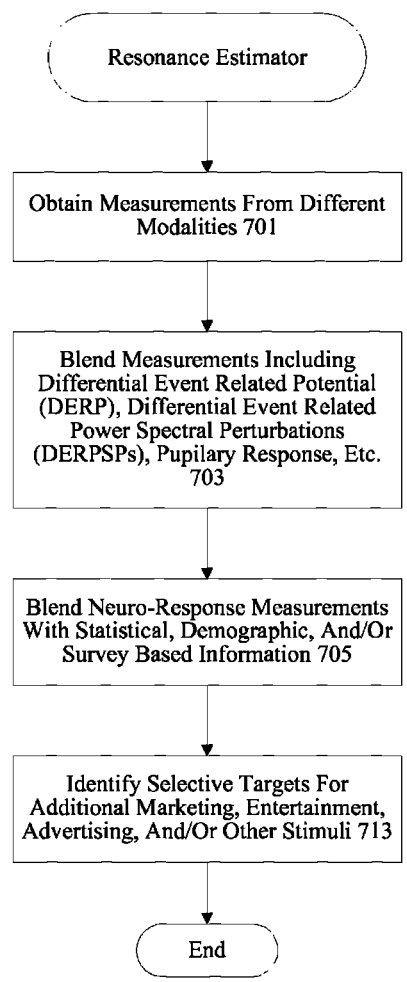
FIG. 7 illustrates one example of technique for estimating stimulus and stimulus attribute resonance.

FIG. 7 illustrates an example of a technique for estimating resonance. According to various embodiments, measurements from different modalities are obtained at 701. According to various embodiments, measurements including Differential Event Related Potential (DERP), Differential Event Related Power Spectral Perturbations (DERPSPs), Pupilary Response, etc., are blended to obtain a combined measurement at 703. In particular embodiments, each measurement may have to be aligned appropriately in order to allow blending. According to various embodiments, a resonance estimator includes mechanisms to use and blend different measures from across the modalities from the data analyzer. In particular embodiments, the data includes the DERP measures, DERPSPs, pupilary response, GSR, eye movement, coherence, coupling and lambda wave based response. Measurements across modalities are blended to elicit a synthesized measure of user resonance.

At 705, neuro-response measurements such as DERP, DERPSPs, pupilary response, etc., are combined with statistical, demographic, and/or survey based information. The device contains mechanisms to integrate the neuro-physiological and neuro-behavioral response with other attributes and meta information on the stimulus (statistical, demographic and/or survey based) for the selection of targets for additional stimulus preparation/presentation at 713.

The resonance estimator can further include an adaptive learning component that refines profiles and tracks variations responses to particular stimuli or series of stimuli over time. This information can be made available for other purposes, such as use of the information for presentation attribute decision making. According to various embodiments, the resonance estimator generates an index for use of evaluation. Data and measurements are stored in a repository for later retrieval and analysis.

According to various embodiments, various mechanisms such as the data collection mechanisms, the intra-modality synthesis mechanisms, cross-modality synthesis mechanisms, etc. are implemented on multiple devices. However, it is also possible that the various mechanisms be implemented in hardware, firmware, and/or software in a single system.

Figure 8:
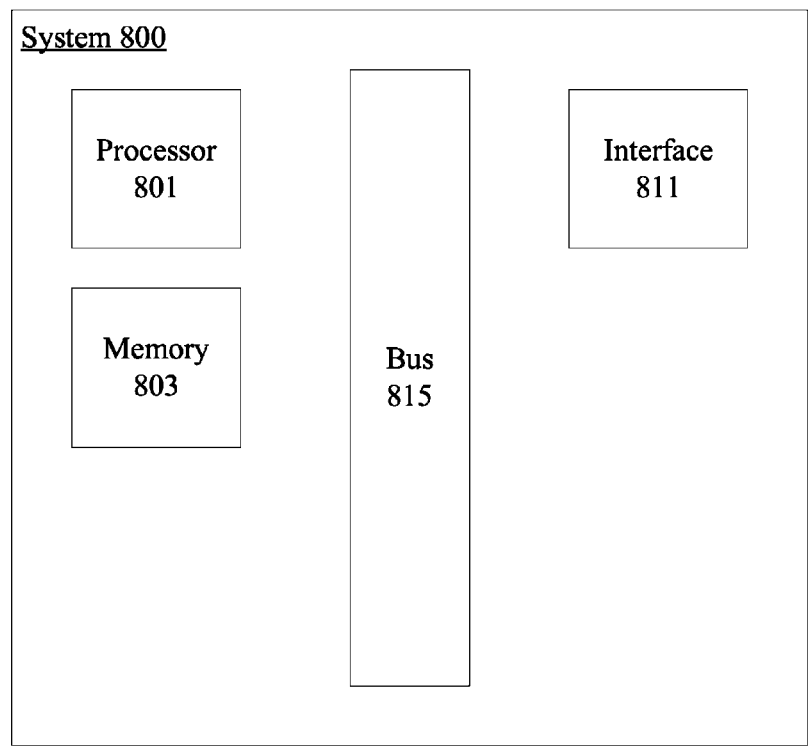
FIG. 8 provides one example of a system that can be used to implement one or more mechanisms.

FIG. 8 provides one example of a system that can be used to implement one or more mechanisms. For example, the system shown in FIG. 8 may be used to implement a resonance measurement system.

According to particular example embodiments, a system 800 suitable for implementing particular embodiments of the present invention includes a processor 801, a memory 803, an interface 811, and a bus 815 (e.g., a PCI bus). When acting under the control of appropriate software or firmware, the processor 801 is responsible for such tasks such as pattern generation. Various specially configured devices can also be used in place of a processor 801 or in addition to processor 801. The complete implementation can also be done in custom hardware. The interface 811 is typically configured to send and receive data packets or data segments over a network. Particular examples of interfaces the device supports include host bus adapter (HBA) interfaces, Ethernet interfaces, frame relay interfaces, cable interfaces, DSL interfaces, token ring interfaces, and the like.

In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as data synthesis.

According to particular example embodiments, the system 800 uses memory 803 to store data, algorithms and program instructions. The program instructions may control the operation of an operating system and/or one or more applications, for example. The memory or memories may also be configured to store received data and process received data.

Because such information and program instructions may be employed to implement the systems/methods described herein, the present invention relates to tangible, machine readable media that include program instructions, state information, etc. for performing various operations described herein. Examples of machine-readable media include, but are not limited to, magnetic media such as hard disks, floppy disks, and magnetic tape; optical media such as CD-ROM disks and DVDs; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Although the foregoing invention has been described in some detail for purposes of clarity of understanding, it will be apparent that certain changes and modifications may be practiced within the scope of the appended claims. Therefore, the present embodiments are to be considered as illustrative and not restrictive and the invention is not to be limited to the details given herein, but may be modified within the scope and equivalents of the appended claims.

What is claimed is:

1. A system, comprising:
    a data collector to obtain first encephalography data from a subject prior to exposure to an advertisement or entertainment and second encephalography data from the subject after exposure to the advertisement or entertainment;
    a data analyzer to:
        detect a first pattern of oscillation in a first frequency band of the second encephalography data,
        detect a second pattern of oscillation in a second frequency band of the second encephalography data,
        identify a first degree of phase synchrony between the first pattern of oscillation from the first frequency band and the second pattern of oscillation from the second frequency band by detecting a repeating sequence of relative phase angles between the first pattern of oscillation in the first frequency band and the second pattern of oscillation in the second frequency band,
        calculate a first event related potential measurement from the first encephalography data,
        calculate a first event related power spectral perturbation from the first encephalography data,
        calculate a second event related potential measurement from the second encephalography data,
        calculate a second event related power spectral perturbation from the second encephalography data,
        calculate a differential event related potential measurement by subtracting the first event related potential measurement from the second event related potential measurement, and
        calculate a differential event related power spectral perturbation based on the first event related power spectral perturbation and the second event related power spectral perturbation; and
    a resonance estimator to determine a resonance measurement to the advertisement or entertainment based on one or more of the first degree of phase synchrony, the differential event related potential measurement or the differential event related power spectral perturbation.

2. The system of claim 1, wherein at least one of the first encephalography data or the second encephalography data includes data from multiple regions of a brain of the subject.

3. The system of claim 1, wherein the data analyzer is to assess at least one of attention, emotion or memory retention based on the differential event related potential measurement.

4. The system of claim 1, wherein the second frequency band is different from the first frequency band.

5. The system of claim 4, wherein the first frequency band comprises one of a theta frequency, an alpha frequency, a beta frequency, a gamma frequency or a high gamma frequency and the second frequency band comprises another one of the theta frequency, the alpha frequency, the beta frequency, the gamma frequency or the high gamma frequency.

6. The system of claim 1, wherein the attribute of the advertisement or entertainment comprises at least one of a communication, a concept, an experience, a message, an image, an audio component, a price or a packaging.

7. The system of claim 1, wherein the data collector is to obtain at least one of pupillary dilation data, galvanic skin response data or heart rate data from the subject.

8. The system of claim 7, wherein the data analyzer is to at least one of align or combine at least one of the first encephalography data or the second encephalography data with at least one of the pupillary dilation data, the galvanic skin response data or the heart rate data.

9. The system of claim 8, wherein the data analyzer is to at least one of time shift or phase shift at least one of the first encephalography data, the second encephalography data, the pupillary dilation data, the galvanic skin response data or the heart rate data to align the at least one of the first encephalography data or the second encephalography data with the at least one of the pupillary dilation data, the galvanic skin response data or the heart rate data.

10. The system of claim 1, wherein the data collector comprises dry electrodes.

11. The system of claim 1,
wherein the data analyzer is to:
detect a third pattern of oscillation in a third frequency band of the first encephalographic data,
detect a fourth pattern of oscillation in a fourth frequency band of the first encephalographic data, and
identify a second degree of phase synchrony between the third pattern of oscillation from the third frequency band and the fourth pattern of oscillation from the fourth frequency band by detecting a repeating sequence of relative phase angles between the third pattern of oscillation in the third frequency band and the fourth pattern of oscillation in the fourth frequency band, and
calculate a differential degree of phase synchrony based on the first degree of phase synchrony and the second degree of phase synchrony; and
wherein the resonance estimator is to determine the resonance measurement to the advertisement or entertainment based on one or more of the differential degree of phase synchrony, the differential event related potential measurement or the differential event related power spectral perturbation.

12. A method, comprising:
analyzing first encephalography data collected from a subject prior to exposure to an advertisement or entertainment and second encephalography data collected from the subject after exposure to the advertisement or entertainment;
detecting a first pattern of oscillation in a first frequency band of the second encephalography data and a second pattern of oscillation in a second frequency band of the second encephalographic data;
identifying a first degree of phase synchrony between the first pattern of oscillation from the first frequency band and the second pattern of oscillation from the second frequency band by detecting a repeating sequence of relative phase angles between the first pattern of oscillation in the first frequency band and the second pattern of oscillation in the second frequency band;
calculating, using a processor, a first event related potential measurement from the first encephalography data;
calculating, using the processor, a first event related power spectral perturbation from the first encephalography data;
calculating, using the processor, a second event related potential measurement from the second encephalography data;
calculating, using the processor, a second event related power spectral perturbation from the second encephalography data;
subtracting, with the processor, the first event related potential measurement from the second event related potential measurement to calculate a differential event related potential measurement;
calculating, using the processor, a differential event related power spectral perturbation based on the first event related power spectral perturbation and the second event related power spectral perturbation; and
determining a subject resonance measurement to the advertisement or entertainment based on one or more of the first degree of phase synchrony, the differential event related potential measurement or the differential event related power spectral perturbation.

13. The method of claim 12, wherein at least one of the first encephalography data or the second encephalography data includes data from multiple regions of a brain of the subject.

14. The method of claim 12 further comprising assessing at least one of attention, emotion or memory retention based on the differential event related potential measurement.

15. The method of claim 12, wherein the second frequency band is different from the first frequency band.

16. The method of claim 12, wherein the attribute of the advertisement or entertainment comprise at least one of a communication, a concept, an experience, a message, an image, an audio component, a price or a packaging.

17. The method of claim 12, wherein the second encephalography data includes data from the first frequency band and the second frequency band representative of brain activity occurring at a same instance in time.

18. The method of claim 12, wherein the second encephalography data includes data from a first hemisphere of the brain and a second hemisphere of the brain.

19. The method of claim 18, wherein the differential event related potential is based on a lateral asymmetry between the first hemisphere and the second hemisphere.

20. The method of claim 12, wherein the first encephalography data and second encephalography data is gathered from a first location of a scalp of the subject.

21. The method of claim 12, wherein the first event related potential is a first signature of amplitudes in the first encephalography data occurring at a first time period and the second event related potential is a second signature of amplitudes in the second encephalography data occurring at a second time period corresponding to the first time period.

22. The method of claim 12, wherein the differential event related potential is based on a coherence between the first encephalography data gathered during a first time period and the second encephalography data gathered during a second time period corresponding to the first time period.

23. The method of 12 further comprising:
detecting a third pattern of oscillation in a third frequency band of the first encephalographic data;
detecting a fourth pattern of oscillation in a fourth frequency band of the first encephalographic data;
identifying a second degree of phase synchrony between the third pattern of oscillation from the third frequency band and the fourth pattern of oscillation from the fourth frequency band by detecting a repeating sequence of relative phase angles between the third pattern of oscillation in the third frequency band and the fourth pattern of oscillation in the fourth frequency band;
calculating a differential degree of phase synchrony based on the first degree of phase synchrony and the second degree of phase synchrony; and
determining the subject resonance measurement to the advertisement or entertainment based on one or more of the differential degree of phase synchrony, the differential event related potential measurement or the differential event related power spectral perturbation.

24. A tangible machine readable storage medium comprising instructions which, when read, cause a machine to at least:
analyze first encephalography data collected from a subject prior to exposure to an advertisement or entertainment and second encephalography data collected from the subject after exposure to the advertisement or entertainment;
detect a first pattern of oscillation in a first frequency band of the second encephalography data;

detect a second pattern of oscillation in a second frequency band of the second encephalography data identify a first degree of phase synchrony between the first pattern of oscillation from the first frequency band and the second pattern of oscillation from the second frequency band by detecting a repeating sequence of relative phase angles between the first pattern of oscillation in the first frequency band and the second pattern of oscillation in the second frequency band;

calculate a first event related potential measurement from the first encephalography data;

calculate a first event related power spectral perturbation from the first encephalography data;

calculate a second event related potential measurement from the second encephalography data;

calculate a second event related power spectral perturbation from the second encephalography data;

subtract the first event related potential measurement from the second event related potential measurement to calculate a differential event related potential measurement;

calculate a differential event related power spectral perturbation based on the first event related power spectral perturbation and the second event related power spectral perturbation; and determine a subject resonance measurement to the advertisement or entertainment based on one or more of the first degree of phase synchrony, the differential event related potential measurement or the differential event related power spectral perturbation.

25. The machine readable medium of claim 24, wherein at least one of the first encephalography data or the second encephalography data includes data from multiple regions of a brain of the subject.

26. The machine readable medium of claim 24 further causing the machine to assess at least one of attention, emotion or memory retention based on the differential event related potential measurement.

27. The machine readable medium of claim 24, wherein the second frequency band is different from the first frequency band.

28. The machine readable medium of claim 24, wherein the attribute of the advertisement or entertainment comprise at least one of a communication, a concept, an experience, a message, an image, an audio component, a price or a packaging.

29. The machine readable medium of claim 24, wherein the instructions further cause the machine to:

detect a third pattern of oscillation in a third frequency band of the first encephalographic data;

detect a fourth pattern of oscillation in a fourth frequency band of the first encephalographic data;

identify a second degree of phase synchrony between the third pattern of oscillation from the third frequency band and the fourth pattern of oscillation from the fourth frequency band by detecting a repeating sequence of relative phase angles between the third pattern of oscillation in the third frequency band and the fourth pattern of oscillation in the fourth frequency band;

calculate a differential degree of phase synchrony based on the first degree of phase synchrony and the second degree of phase synchrony; and determine the subject resonance measurement to the advertisement or entertainment based on one or more of the differential degree of phase synchrony, the differential event related potential measurement or the differential event related power spectral perturbation.

* * * * *